(12) United States Patent
Presta

(10) Patent No.: US 8,637,019 B2
(45) Date of Patent: Jan. 28, 2014

(54) ENGINEERED ANTI-TSLP ANTIBODY

(75) Inventor: Leonard G. Presta, San Francisco, CA (US)

(73) Assignee: Merck Sharp & Dohme Corp., Rahway, NJ (US)

(*) Notice: Subject to any disclaimer, the term of this patent is extended or adjusted under 35 U.S.C. 154(b) by 0 days.

(21) Appl. No.: 13/505,340

(22) PCT Filed: Nov. 2, 2010

(86) PCT No.: PCT/US2010/055062
§ 371 (c)(1),
(2), (4) Date: May 1, 2012

(87) PCT Pub. No.: WO2011/056772
PCT Pub. Date: May 12, 2011

(65) Prior Publication Data
US 2012/0219565 A1    Aug. 30, 2012

Related U.S. Application Data

(60) Provisional application No. 61/297,008, filed on Jan. 21, 2010, provisional application No. 61/258,051, filed on Nov. 4, 2009.

(51) Int. Cl.
*A61K 39/395* (2006.01)
*C12N 15/13* (2006.01)
*C12P 21/08* (2006.01)

(52) U.S. Cl.
USPC ............... 424/133.1; 424/145.1; 530/388.23; 530/351; 435/69.6; 435/320.1; 435/252.3; 435/325; 536/23.53

(58) Field of Classification Search
None
See application file for complete search history.

(56) References Cited

U.S. PATENT DOCUMENTS

| | | | |
|---|---|---|---|
| 6,555,520 | B2 | 4/2003 | Sims et al. |
| 7,304,144 | B2 | 12/2007 | Sims et al. |
| 7,405,058 | B2 | 7/2008 | Sims et al. |
| 2005/0249712 | A1 | 11/2005 | Leonard et al. |
| 2006/0171943 | A1 | 8/2006 | Comeau et al. |
| 2006/0198822 | A1 | 9/2006 | Booth et al. |

FOREIGN PATENT DOCUMENTS

| | | |
|---|---|---|
| EP | 1593690 | 11/2005 |
| EP | 1129190 | 5/2007 |
| JP | 2008109915 | 5/2008 |
| WO | WO92/11018 | 7/1992 |
| WO | WO00/39149 | 7/2000 |
| WO | WO03/032898 | 4/2003 |
| WO | WO03/065985 | 8/2003 |
| WO | WO2006/023791 | 3/2006 |
| WO | WO2007/045996 | 4/2007 |
| WO | WO2007/096149 | 8/2007 |
| WO | WO2008/012645 | 1/2008 |
| WO | WO2008/066444 | 6/2008 |
| WO | WO2008/076321 | 6/2008 |
| WO | WO2009/035577 | 3/2009 |

OTHER PUBLICATIONS

Davies J. et al.: "Affinity Improvement of Single Antibody VH Domains: Residues In Ali Three Hypervariable Regions Affect Antigen Binding," Immunotechnology, Elsevier Science Publishers BV, NL, vol. 2, No. 3, Sep. 1996, pp. 169-179.
Holt L. J. et al. "Domain Antibodies: Proteins for Therapy," Trends In Biotechnology, Elsevier Publications, Cambridge, GB, vol. 21, No. 11, Nov. 2003, pp. 484-490.
Online: "Anti-Human TSLP Antibody AF1398," Internet Citation, Feb. 15, 2006, Retrieved from the Internet: URL: http://www.rndsystems.com/pdf/af1398.pdf.
Online: "Monoclonal Anti-Human TSLP Antibody," Internet Citation, Aug. 6, 2005, Retrieved from the Internet: URL: http://www.rndsystems.com/pdf/MAB1398.pdf.
Soumelis V. et al.: "Human Epithelial Cells Trigger Dendritic Cell Mediated Allergic Inflammation by Producing TSLP," Nature Immunology, Nature Publishing Group, GB, vol. 3. No. 7 Jul. 2002, pp. 673-680.
Soumelis V. et al.: "Human Thymic Stromal Lymphopoientin: A Novel Epithelial Cell-Derived Cytokine and A Potential Key Player in the Induction of Allergic Inflammation," Springer Seminar in Immunopathology, Springer Verlag, DE, vol. 25, No. 3-4, Feb. 2004, pp. 325-333.
International Search Report for PCT/US2007/025531, 5 pages.
William E. Paul, M.D., ed., 3° ed; Fundamental Immunology p. 242 (1993).

*Primary Examiner* — Dong Jiang
(74) *Attorney, Agent, or Firm* — Sheela Mohan-Peterson

(57) ABSTRACT

The invention relates to binding compounds that specifically bind to human TSLP, as well as uses thereof, e.g., in the treatment of inflammatory disorders and allergic inflammatory response.

15 Claims, 1 Drawing Sheet

```
Sequence 1    20 QVQLVQSGAEVKKPGASVKVSCKASGYIFTDYAMHWVRQAPGQGLEWMGTFIPLLDTSDY
Sequence 2     1 QVQLVQSGAEVKKPGASVKVSCKASGYIFTDYAMHWVRQAPGQGLEWMGTFIPLLDTSDY
                 ************************************************************

Sequence 1    80 AQKFQGRVTMTADTSTSTAYMELRSLRSDDTAVYYCARMGVTHSYVMDAWGQGTLVTVSS
Sequence 2    61 NQNFKGRVTMTTDTSTSTAYMELRSLRSDDTAVYYCARMGVTHSYVMDAWGQGTLVTVSS
                 * *  ******* ***********************************************

Sequence 1   140 ASTKGPSVFPLAPSSKSTSGGTAALGCLVKDYFPEPVTVSWNSGALTSGVHTFPAVLQSS
Sequence 2   121 ASTKGPSVFPLAPSSKSTSGGTAALGCLVKDYFPEPVTVSWNSGALTSGVHTFPAVLQSS
                 ************************************************************

Sequence 1   200 GLYSLSSVVTVPSSSLGTQTYICNVNHKPSNTKVDKKVEPKSCDKTHTCPPCPAPELLGG
Sequence 2   181 GLYSLSSVVTVPSSSLGTQTYICNVNHKPSNTKVDKKVEPKSCDKTHTCPPCPAPELLGG
                 ************************************************************

Sequence 1   260 PSVFLFPPKPKDTLMISRTPEVTCVVVDVSHEDPEVKFNWYVDGVEVHNAKTKPREEQYN
Sequence 2   241 PSVFLFPPKPKDTLMISRTPEVTCVVVDVSHEDPEVKFNWYVDGVEVHNAKTKPREEQYN
                 ************************************************************

Sequence 1   320 STYRVVSVLTVLHQDWLNGKEYKCKVSNKALPAPIEKTISKAKGQPREPQVYTLPPSRDE
Sequence 2   301 STYRVVSVLTVLHQDWLNGKEYKCKVSNKALPAPIEKTISKAKGQPREPQVYTLPPSRDE
                 ************************************************************

Sequence 1   380 LTKNQVSLTCLVKGFYPSDIAVEWESNGQPENNYKTTPPVLDSDGSFFLYSKLTVDKSRW
Sequence 2   361 LTKNQVSLTCLVKGFYPSDIAVEWESNGQPENNYKTTPPVLDSDGSFFLYSKLTVDKSRW
                 ************************************************************

Sequence 1   440 QQGNVFSCSVMHEALHNHYTQKSLSLSPGK
Sequence 2   421 QQGNVFSCSVMHEALHNHYTQKSLSLSPGK
                 ******************************
```

ENGINEERED ANTI-TSLP ANTIBODY

This application claims the benefit of U.S. provisional patent application no. 61/297,008; filed Jan. 21, 2010; and, U.S. provisional patent application no. 61/258,051; filed Nov. 4, 2009; each of which is herein incorporated by reference in its entirety.

FIELD OF THE INVENTION

The present invention relates generally to a thymic stromal lymphopoietin (TSLP) specific antibody, and uses thereof, particularly in inflammatory, and allergic inflammatory disorders.

BACKGROUND OF THE INVENTION

TSLP is an immune cytokine that induces dendritic cell-mediated $CD4^+$ T cell responses with a proallogenic phenotype DC activated by TSLP play crucial role in the induction and maintenance of allergic inflammatory Th2 and mast cell responses by production of proallergenic cytokines, chemokines and costimulatory molecules that direct naïve T cells to become Th2 cells, producing 11-4, IL-5 and IL-13 critical mediators of allergic inflammation. Over-expression of TSLP in Atopic Dermatitis (AtD), Netherton Syndrome and Asthma indicates a crucial, role of this cytokine in the pathogenesis of these allergic inflammatory diseases. This is supported by animal models in which transgenic over-expression of TSLP in skin or lung as well as removal by gene targeting of negative regulators of TSLP results in allergic inflammatory diseases that closely resemble human atopic dermatitis or Asthma. The present invention provides engineered TSLP antibodies and uses thereof to treat inflammatory, and particularly allergic inflammatory disorders, including asthma and atopic dermatitis.

The present invention avoids potential deamidation problems of prior art antibodies. Deamidation of Asn (N) residues is a common degradation of proteins, and it can significantly impact protein structure and function. In antibodies, Asn (N) located in the CDRs can undergo deamidation rapidly and can result in changes in antibody-antigen interactions and therefore represents a serious concern during the development of antibody-based therapeutics. See, e.g., Vlaska et al., *Analytical Biochemistry* 392:145-154 (2009). Thus, it is important to avoid these potential deamidation problems in antibodies that are intended to be developed for human use. Further, it is important to avoid these problems without changing any of the important characteristics (such as binding affinity) of the antibody.

SUMMARY OF THE INVENTION

The present invention provides a binding compound that specifically binds human TSLP, comprising at least one antibody heavy chain variable region, or a TSLP-binding fragment thereof, said heavy chain variable region comprising SEQ ID NO:2

The present invention also provides a binding compound that specifically binds human TSLP comprising at least one antibody heavy chain variable region, or a TSLP-binding fragment thereof, said heavy chain variable region comprising at least SEQ ID NO:2 and SEQ ID NO:1, or SEQ ID NO:2 and SEQ ID NO:3.

The present invention also provides a binding compound that specifically binds human TSLP comprising at least one antibody heavy chain variable region, or a TSLP-binding fragment thereof, said heavy chain variable region comprising SEQ ID NO: 1, SEQ ID NO:2, and SEQ ID NO:3.

The binding compounds of the invention could further comprise one antibody light chain variable region, or a TSLP-binding fragment thereof. In one embodiment, the antibody light chain variable region, or a TSLP-binding fragment thereof, comprises at least one sequence selected from the group consisting of SEQ ID NOs: 4, 5 and 6. In another embodiment, the antibody light chain variable region, or TSLP-binding fragment thereof, comprises at least two sequences selected from the group consisting of SEQ ID NOs: 4, 5 and 6. In other embodiments, the antibody light chain variable region, or TSLP-binding fragment thereof, has the three sequences set forth in SEQ ID NOs: 4, 5 and 6.

In some embodiments of the above described binding compounds, all or substantially all of the remainder of the heavy chain variable region is all or substantially all a human Ig region; and all or substantially all of the remainder of the light chain variable region variable region is all or substantially all a human Ig region. In preferred embodiments, the remainder of the heavy chain variable region is human heavy chain amino acid sequence; and the remainder of the light chain variable region is human light chain amino acid sequence.

The present invention also provides a binding compound that specifically binds human TSLP, comprising: a heavy chain variable region comprising a sequence selected from the group consisting of: (i) SEQ ID NO: 7; (ii) SEQ ID NO:7 or a variant comprising up to 3 modified amino acid residues; and (iii) a sequence having at least 97% homology to SEQ ID NO: 7. In one embodiment, the heavy chain variable region comprises the sequence shown in SEQ ID NO:7. In some embodiments, the binding compound of the invention further comprises a light chain variable region. In one embodiment the light chain variable region comprises a sequence selected from the group consisting of: (i) SEQ ID NO: 8; (ii) SEQ ID NO:8 or a variant variant comprising up to 3 modified amino acid residues; and (iii) a sequence having at least 97% homology to SEQ ID NO: 8. In one embodiment, the light chain variable region comprises the sequence shown in SEQ ID NO:8.

In a preferred embodiment, the binding compound comprises a heavy chain variable region comprising the sequence shown in SEQ ID NO:7 and a light chain variable region comprising the sequence shown in SEQ ID NO:8.

In some embodiments, the binding compounds of the invention also comprise a heavy chain constant region and/or a light chain constant region. In some embodiment, the heavy chain constant region comprises a γ1, γ2, γ3, or γ4 human heavy chain constant region or a variant thereof. In other embodiments the light chain constant region comprises a lambda or a kappa human light chain constant region.

In some embodiments, the binding compound of the invention is an antibody or an antigen binding fragment thereof. In various embodiments the antibody or fragment thereof of the present invention is polyclonal, monoclonal, chimeric, cynoized, humanized or fully human. In a preferred embodiment, the antibody is a humanized antibody or a fragment thereof.

The present invention also contemplates that the binding fragment is an antibody fragment selected from the group consisting of Fab, Fab', Fab'-SH, Fv, scFv, F(ab')$_2$, and a diabody. The present invention also contemplates that the binding compound is a nanobody, an avimer, or an aptimer.

In one embodiment, the binding compound is an antibody comprising a heavy chain comprising SEQ ID NO:11. In one embodiment, the binding compound comprises a heavy chain comprising SEQ ID NO:11 and a light chain comprising SEQ ID NO:12.

In another preferred embodiment, the binding compound of the invention binds human and cyno TSLP.

In one embodiment, the binding compound of the invention can be expressed from the expression vector deposited at the American Type Culture Collection (10801 University Blvd., Manassas, Va. 20110-2209 USA) ("ATCC") with the patent deposit designation PTA-10482. The vector was deposited on Nov. 17, 2009 under the conditions of the Budapest Treaty.

In another embodiment, the binding compound of the invention comprises a heavy chain and a light chain that can be expressed from the expression vector deposited under ATCC Deposit No. PTA-10482. In another embodiment, the binding compound of the invention comprises a heavy chain variable region and a light chain variable region that can be expressed from the expression vector deposited under ATCC Deposit No. PTA-10482. In another embodiment, the binding compound of the invention comprises the CDR-H1, CDR-H2 and CDR-H3 and the CDR-L1, CDR-L2 and CDR-L3 regions of the antibody expressed by the expression vector deposited under ATCC Deposit No. PTA-10482

In another embodiment, the binding compound of the invention comprises a heavy chain that can be expressed from the expression vector deposited under ATCC Deposit No. PTA-10482. In another embodiment, the binding compound of the invention comprises a heavy chain variable region that can be expressed from the expression vector deposited under ATCC Deposit No. PTA-10482. In another embodiment, the binding compound of the invention comprises the CDR-H1, CDR-H2 and CDR-H3 regions of the antibody expressed by the expression vector deposited under ATCC Deposit No. PTA-10482.

The present invention also provides isolated nucleic acids encoding the binding compound of the invention. In one embodiment, the invention comprises a nucleic acid encoding a heavy chain variable region of a binding compound (for example an antibody or antibody fragment) of the invention. In another embodiment, the invention comprises a nucleic acid encoding a binding compound comprising a heavy chain variable region, wherein said heavy chain variable region comprises SEQ ID NO:1, SEQ ID NO:2 and SEQ ID NO:3. In another embodiment, the invention comprises a nucleic acid encoding SEQ ID NO:7. In another embodiment, the invention comprises a nucleic acid encoding SEQ ID NO:2. In one embodiment, the invention comprises a nucleic acid encoding the heavy chain variable region encoded by the expression vector deposited under ATCC Deposit No. PTA-10482. The invention also provides for expression vectors comprising the nucleic acids of the invention operably linked to control sequences that are recognized by a host cell when the host cell is transfected with the vector. In one embodiment, the invention provides the expression vector deposited under ATCC Deposit No. PTA-10482. Also provided are host cells comprising these expression vectors, and methods of using these expression vectors for producing polypeptides. In one embodiment, the host cell comprises the expression vector deposited under ATCC Deposit No. PTA-10482. The methods of producing polypeptide comprise the steps of: culturing the host cell of in culture medium under conditions wherein the nucleic acid sequence is expressed, thereby producing polypeptides comprising the light and heavy chain variable regions; and recovering the polypeptides from the host cell or culture medium. In one embodiment, the invention comprises a method of producing a polypeptide comprising the steps of: culturing a host cell comprising the expression vector deposited under ATCC Deposit No. PTA-10482 in culture medium under conditions wherein the vector is expressed, thereby producing polypeptides comprising the light and heavy chain variable regions; and recovering the polypeptides from the host cell or culture medium.

The present invention encompasses a method of suppressing an immune response in a human subject comprising administering to a subject in need thereof a binding compound according to the invention that specifically binds human TSLP, in an amount effective to block the biological activity of TSLP. The present invention also contemplates administering an additional immunosuppressive or anti-inflammatory agent. In a preferred embodiment, the immune response is asthma. In another preferred embodiment, the immune response is allergic inflammation. In another preferred embodiment, the allergic inflammation is allergic rhinosinusitis, allergic asthma, allergic conjunctivitis, or atopic dermatitis. In another preferred embodiment, the immune response is fibrosis, inflammatory bowel disease or Hodgkin's lymphoma. In another preferred embodiment, the binding compound is administered in combination with another immunomodulatory agent.

The binding compound the present invention can be in a composition comprising the binding compound of the invention (for example an antibody or a fragment thereof) in combination with a pharmaceutically acceptable carrier or diluent. In a further embodiment, the composition further comprises an immunosuppressive or anti-inflammatory agent.

In various embodiments, the invention relates to medicaments comprising the binding compound (for example an antibody or fragment thereof) of the present invention. For example, the invention encompasses the use of a binding compound that specifically binds human TSLP for the preparation of a medicament to suppress an immune response. The present invention encompasses the use of a binding compound that specifically binds human TSLP (for example, any one of the binding compounds according to the invention) for the preparation of a medicament to treat asthma. The present invention encompasses the use of a binding compound that specifically binds human TSLP for the preparation of a medicament to treat an inflammatory disorder. In one embodiment, the inflammatory disorder is an allergic inflammatory disorder. In one embodiment, the allergic inflammatory disorder is allergic rhinosinusitis, allergic asthma, allergic conjunctivitis, or atopic dermatitis. In a preferred embodiment the allergic inflammatory disorder is allergic asthma. In another preferred embodiment, the allergic inflammatory disorder is atopic dermatitis. For example, the antibodies and fragment of the present invention may be used to treat humans.

BRIEF DESCRIPTION OF THE FIGURE

FIG. 1. Alignment of SEQ ID NO:11 of the instant application against SEQ ID NO:14 of WO2008/076321.

DETAILED DESCRIPTION

As used herein, including the appended claims, the singular forms of words such as "a," "an," and "the," include their corresponding plural references unless the context clearly dictates otherwise. All references cited herein are incorporated by reference to the same extent as if each individual publication, patent application, or patent, was specifically and individually indicated to be incorporated by reference.

I. Definitions

"Activation," "stimulation," and "treatment," as it applies to cells or to receptors, may have the same meaning, e.g., activation, stimulation, or treatment of a cell or receptor with a ligand, unless indicated otherwise by the context or explicitly. "Ligand" encompasses natural and synthetic ligands, e.g., cytokines, cytokine variants, analogues, muteins, and binding compositions derived from antibodies. "Ligand" also encompasses small molecules, e.g., peptide mimetics of cytokines and peptide mimetics of antibodies. "Activation" can refer to cell activation as regulated by internal mechanisms as well as by external or environmental factors. "Response," e.g., of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming.

"Activity" of a molecule may describe or refer to the binding of the molecule to a ligand or to a receptor, to catalytic activity; to the ability to stimulate gene expression or cell signaling, differentiation, or maturation; to antigenic activity, to the modulation of activities of other molecules, and the like. "Activity" can also mean specific activity, e.g., [catalytic activity]/[mg protein], or [immunological activity]/[mg protein], concentration in a biological compartment, or the like.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. "Administration" and "treatment" can refer, e.g., to therapeutic, pharmacokinetic, diagnostic, research, and experimental methods. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding composition, or by another cell. "Treatment," as it applies to a human, veterinary, or research subject, refers to therapeutic treatment, prophylactic or preventative measures, to research and diagnostic applications.

"Binding compound" refers to a molecule that comprises one or more amino acid sequences that specifically bind to human TSLP. In one preferred embodiment, the binding compound is an antibody, preferably an isolated antibody. In another preferred embodiment, the binding compound comprises an antigen-binding fragment of an antibody.

"Binding composition" refers to a TSLP-binding compound in combination with a stabilizer, excipient, salt, buffer, solvent, or additive, capable of binding to a target.

The scope of the present invention also includes complexes comprising any antibody or antigen-binding fragment thereof of the present invention complexed with TSLP polypeptide or an antigenic fragment thereof. Complexes may be prepared by contacting the antibody or fragment with the TSLP polypeptide or antigen fragment.

As used herein, the term "antibody" refers to any form of antibody or fragment thereof that exhibits the desired biological activity. Thus, it is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity. "Isolated antibody" refers to the purification status of a binding compound and in such context means the molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

A "Fab fragment" is comprised of one light chain and the CH1 and variable regions of one heavy chain. The heavy chain of a Fab molecule cannot form a disulfide bond with another heavy chain molecule.

An "Fc" region contains two heavy chain fragments comprising the CH2 and CH3 domains of an antibody. The two heavy chain fragments are held together by two or more disulfide bonds and by hydrophobic interactions of the CH3 domains.

A "Fab' fragment" contains one light chain and a portion or fragment of one heavy chain that contains the VH domain and the CH1 domain and also the region between the CH1 and CH2 domains, such that an interchain disulfide bond can be formed between the two heavy chains of two Fab' fragments to form a F(ab') 2 molecule.

A "F(ab')2 fragment" contains two light chains and two heavy chains containing a portion of the constant region between the CH1 and CH2 domains, such that an interchain disulfide bond is formed between the two heavy chains. A F(ab') 2 fragment thus is composed of two Fab' fragments that are held together by a disulfide bond between the two heavy chains.

The "Fv region" comprises the variable regions from both the heavy and light chains, but lacks the constant regions.

As used herein, the term "TSLP binding fragment" or "binding fragment thereof" encompasses a fragment or a derivative of an antibody (or another binding substance) that still substantially retain its biological activity of inhibiting TSLP activity. Therefore, the term "antibody fragment" or TSLP binding fragment refers to a portion of a full length antibody, generally the antigen binding or variable region thereof. Examples of antibody fragments include Fab, Fab', F(ab')$_2$, and Fv fragments; diabodies; linear antibodies; single-chain antibody molecules, e.g., sc-Fv; domain antibodies; and multispecific antibodies formed from antibody fragments. Typically, a binding fragment or derivative retains at least 10% of its TSLP inhibitory activity. Preferably, a binding fragment or derivative retains at least 25%, 50%, 60%, 70%, 80%, 90%, 95%, 99% or 100% (or more) of its TSLP inhibitory activity, although any binding fragment with sufficient affinity to exert the desired biological effect will be useful. It is also intended that a TSLP binding fragment can include conservative amino acid substitutions that do not substantially alter its biologic activity.

The term "monoclonal antibody", as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. In contrast, conventional (polyclonal) antibody preparations typically include a multitude of antibodies directed against (or specific for) different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., (1975) Nature 256: 495, or may be made by recombinant DNA methods (see, e.g., U.S. Pat. No. 4,816,567). The "monoclonal antibodies" may also be isolated from phage antibody libraries using the techniques described in Clackson et al., (1991) *Nature* 352: 624-628 and Marks et al., (1991) *J. Mol. Biol.* 222: 581-597, for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., (1984) *Proc. Natl. Acad. Sci. USA* 81: 6851-6855).

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

A "bivalent antibody" comprises two antigen binding sites. In some instances, the two binding sites have the same antigen specificities. However, bivalent antibodies may be bispecific.

As used herein, the term "single-chain Fv" or "scFv" antibody refers to antibody fragments comprising the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv, see Pluckthun (1994) THE PHARMACOLOGY OF MONOCLONAL ANTIBODIES, vol. 113, Rosenburg and Moore eds. Springer-Verlag, New York, pp. 269-315.

The monoclonal antibodies herein also include camelized single domain antibodies. See, e.g., Muyldermans et al. (2001) *Trends Biochem. Sci.* 26:230; Reichmann et al. (1999) *J. Immunol. Methods* 231:25; WO 94/04678; WO 94/25591; U.S. Pat. No. 6,005,079, which are hereby incorporated by reference in their entireties). In one embodiment, the present invention provides single domain antibodies comprising two $V_H$ domains with modifications such that single domain antibodies are formed.

As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al. (1993) *Proc. Natl. Acad. Sci. USA* 90: 6444-6448. For a review of engineered antibody variants generally see Holliger and Hudson (2005) *Nat. Biotechnol.* 23:1126-1136.

As used herein, the term "humanized antibody" refers to forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The prefix "h", "hu" or "hum" is added to antibody clone designations when necessary to distinguish humanized antibodies (e.g., "hu23B12") from parental rodent antibodies (e.g., rat 23B12, or "r23B12"). The humanized forms of rodent antibodies will generally comprise the same CDR sequences of the parental rodent antibodies, although certain amino acid substitutions may be included to increase affinity or increase stability of the humanized antibody.

The antibodies of the present invention also include antibodies with modified (or blocked) Fc regions to provide altered effector functions. See, e.g., U.S. Pat. No. 5,624,821; WO2003/086310; WO2005/120571; WO2006/0057702; Presta (2006) *Adv. Drug Delivery Rev.* 58:640-656. Such modification can be used to enhance or suppress various reactions of the immune system, with possible beneficial effects in diagnosis and therapy. Alterations of the Fc region include amino acid changes (substitutions, deletions and insertions), glycosylation or deglycosylation, and adding multiple Fc. Changes to the Fc can also alter the half-life of antibodies in therapeutic antibodies, and a longer half-life would result in less frequent dosing, with the concomitant increased convenience and decreased use of material. See Presta (2005) *J. Allergy Clin. Immunol.* 116:731 at 734-35.

The term "fully human antibody" refers to an antibody that comprises human immunoglobulin protein sequences only. A fully human antibody may contain murine carbohydrate chains if produced in a mouse, in a mouse cell, or in a hybridoma derived from a mouse cell. Similarly, "mouse antibody" refers to an antibody which comprises mouse immunoglobulin sequences only.

As used herein, the term "hypervariable region" refers to the amino acid residues of an antibody that are responsible for antigen-binding. The hypervariable region comprises amino acid residues from a "complementarity determining region" or "CDR" (e.g. residues 24-34 (CDRL1), 50-56 (CDRL2) and 89-97 (CDRL3) in the light chain variable domain and residues 31-35 (CDRH1), 50-65 (CDRH2) and 95-102 (CDRH3) in the heavy chain variable domain; Kabat et al., (1991) Sequences of Proteins of Immunological Interest, 5th Ed. Public Health Service, National Institutes of Health, Bethesda, Md.) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, (1987) *J. Mol. Biol.* 196: 901-917). As used herein, the term "framework" or "FR" residues refers to those variable domain residues other than the hypervariable region residues defined herein as CDR residues. The residue numbering above relates to the Kabat numbering system and does not necessarily correspond in detail to the sequence numbering in the accompanying Sequence Listing.

"Binding" refers to an association of the binding composition with a target where the association results in reduction in the normal Brownian motion of the binding composition, in cases where the binding composition can be dissolved or suspended in solution.

"Conservatively modified variants" or "conservative substitution" refers to substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson, et al., *Molecular Biology of the Gene*, The Benjamin/Cummings Pub. Co., p. 224 (4th Edition 1987)). Such exemplary substitutions are preferably made in accordance with those set forth in Table 1 as follows:

TABLE 1

Exemplary Conservative Amino Acid Substitutions

| Original residue | Conservative substitution |
|---|---|
| Ala (A) | Gly; Ser |
| Arg (R) | Lys, His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

"Effective amount" encompasses an amount sufficient to ameliorate or prevent a symptom or sign of the medical condition. Effective amount also means an amount sufficient to allow or facilitate diagnosis. An effective amount for a particular patient or veterinary subject may vary depending on factors such as the condition being treated, the overall health of the patient, the method route and dose of administration and the severity of side affects (see, e.g., U.S. Pat. No. 5,888,530 issued to Netti, et al.). An effective amount can be the maximal dose or dosing protocol that avoids significant side effects or toxic effects. The effect will result in an improvement of a diagnostic measure or parameter by at least 5%, usually by at least 10%, more usually at least 20%, most usually at least 30%, preferably at least 40%, more preferably at least 50%, most preferably at least 60%, ideally at least 70%, more ideally at least 80%, and most ideally at least 90%, where 100% is defined as the diagnostic parameter shown by a normal subject (see, e.g., Maynard, et al. (1996) *A Handbook of SOPs for Good Clinical Practice*, Interpharm Press, Boca Raton, Fla.; Dent (2001) *Good Laboratory and Good Clinical Practice*, Urch Publ., London, UK).

As used herein, the term "isolated nucleic acid molecule" refers to a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

As used herein, "polymerase chain reaction" or "PCR" refers to a procedure or technique in which minute amounts of a specific piece of nucleic acid, RNA and/or DNA, are amplified as described in, e.g., U.S. Pat. No. 4,683,195. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers can coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al. (1987) *Cold Spring Harbor Symp. Quant. Biol.* 51:263; Erlich, ed., (1989) PCR TECHNOLOGY (Stockton Press, N.Y.) As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

As used herein, the term "germline sequence" refers to a sequence of unrearranged immunoglobulin DNA sequences. Any suitable source of unrearranged immunoglobulin DNA may be used.

"Inhibitors" are compounds that decrease, block, prevent, delay activation, inactivate, desensitize, or down regulate, e.g., a gene, protein, ligand, receptor, or cell. An inhibitor may also be defined as a composition that reduces, blocks, or inactivates a constitutive activity. An "antagonist" is a compound that opposes the actions of an agonist. An antagonist prevents, reduces, inhibits, or neutralizes the activity of an agonist. An antagonist can also prevent, inhibit, or reduce constitutive activity of a target, e.g., a target receptor, even where there is no identified agonist.

To examine the extent of inhibition, for example, samples or assays comprising a given, e.g., protein, gene, cell, or organism, are treated with a potential activating or inhibiting agent and are compared to control samples without the agent. Control samples, i.e., not treated with agent, are assigned a relative activity value of 100% Inhibition is achieved when the activity value relative to the control is about 90% or less, typically 85% or less, more typically 80% or less, most typically 75% or less, generally 70% or less, more generally 65% or less, most generally 60% or less, typically 55% or less, usually 50% or less, more usually 45% or less, most usually 40% or less, preferably 35% or less, more preferably 30% or less, still more preferably 25% or less, and most preferably less than 25%.

Endpoints in inhibition can be monitored as follows. Inhibition, and response to treatment, e.g., of a cell, physiological fluid, tissue, organ, and animal or human subject, can be monitored by an endpoint. The endpoint may comprise a predetermined quantity or percentage of, e.g., an indicia of inflammation, oncogenicity, or cell degranulation or secretion, such as the release of a cytokine, toxic oxygen, or a protease. The endpoint may comprise, e.g., a predetermined quantity of ion flux or transport; cell migration; cell adhesion; cell proliferation; potential for metastasis; cell differentiation; and change in phenotype, e.g., change in expression of gene relating to inflammation, apoptosis, transformation, cell cycle, or metastasis (see, e.g., Knight (2000) *Ann. Clin. Lab. Sci.* 30:145-158; Hood and Cheresh (2002) *Nature Rev. Cancer* 2:91-100; Timme, et al. (2003) *Curr. Drug Targets* 4:251-261; Robbins and Itzkowitz (2002) *Med. Clin. North Am.* 86:1467-1495; Grady and Markowitz (2002) *Annu. Rev. Genomics Hum. Genet.* 3:101-128; Bauer, et al. (2001) *Glia* 36:235-243; Stanimirovic and Satoh (2000) *Brain Pathol.* 10:113-126).

An endpoint of inhibition is generally 75% of the control or less, preferably 50% of the control or less, more preferably 25% of the control or less, and most preferably 10% of the control or less. Generally, an endpoint of activation is at least 150% the control, preferably at least two times the control, more preferably at least four times the control, and most preferably at least 10 times the control.

"Specifically" or "selectively" binds, when referring to a ligand/receptor, antibody/antigen, or other binding pair, indicates a binding reaction which is determinative of the presence of the protein, e.g., TSLP, in a heterogeneous population of proteins and/or other biologics. Thus, under designated conditions, a specified ligand/antigen binds to a particular receptor/antibody and does not bind in a significant amount to other proteins present in the sample.

The antibody, or binding composition derived from the antigen-binding site of an antibody, of the contemplated method binds to its antigen with an affinity that is at least ten times greater, more preferably at least 20-times greater, and most preferably at least 50-times greater than the affinity with unrelated antigens. In a preferred embodiment the antibody will have an affinity that is greater than about $10^9$ liters/mol, as determined, e.g., by Scatchard analysis (Munsen, et al. (1980) *Analyt. Biochem.* 107:220-239).

As used herein, the term "inflammatory disorder" refers to any disease or disorder characterized by local inflammation at a site of injury or infection and includes, without limitation, allergic inflammation, autoimmune diseases, and other disorders characterized by undesired immune cell accumulation at a local tissue site.

As used herein, the term "immunomodulatory agent" refers to natural or synthetic agents that suppress or modulate an immune response. The immune response can be a humoral or cellular response. Immunomodulatory agents encompass immunosuppressive or anti-inflammatory agents.

"Immunosuppressive agents," "immunosuppressive drugs," or "immunosuppressants" as used herein are therapeutics that are used in immunosuppressive therapy to inhibit or prevent activity of the immune system. Clinically they are used to prevent the rejection of transplanted organs and tissues (e.g. bone marrow, heart, kidney, liver), and/or in the treatment of autoimmune diseases or diseases that are most likely of autoimmune origin (e.g. rheumatoid arthritis, myasthenia gravis, systemic lupus erythematosus, ulcerative colitis, multiple sclerosis). Immunosuppressive drugs can be classified into four groups: glucocorticoids cytostatics; antibodies (including Biological Response Modifiers or DMARDs); drugs acting on immunophilins; other drugs, including known chemotherapeutic agents used in the treatment of proliferative disorders. For multiple sclerosis, in particular, the antibodies of the present invention can be administered in conjunction with a new class of myelin binding protein-like therapeutics, known as copaxones.

"Anti-inflammatory agents" or "anti-inflammatory drugs", is used to represent both steroidal and non-steroidal therapeutics. Steroids, also known as corticosteroids, are drugs that closely resemble cortisol, a hormone produced naturally by adrenal glands. Steroids are used as the main treatment for certain inflammatory conditions, such as: Systemic vasculitis (inflammation of blood vessels); and Myositis (inflammation of muscle). Steroids might also be used selectively to treat inflammatory conditions such as: rheumatoid arthritis (chronic inflammatory arthritis occurring in joints on both sides of the body); systemic lupus erythematosus (a generalized disease caused by abnormal immune system function); Sjögren's syndrome (chronic disorder that causes dry eyes and a dry mouth).

Non-steroidal anti-inflammatory drugs, usually abbreviated to NSAIDs, are drugs with analgesic, antipyretic and anti-inflammatory effects—they reduce pain, fever and inflammation. The term "non-steroidal" is used to distinguish these drugs from steroids, which (amongst a broad range of other effects) have a similar eicosanoid-depressing, anti-inflammatory action. NSAIDs are generally indicated for the symptomatic relief of the following conditions: rheumatoid arthritis; osteoarthritis; inflammatory arthropathies (e.g. ankylosing spondylitis, psoriatic arthritis, Reiter's syndrome); acute gout; dysmenorrhoea; metastatic bone pain; headache and migraine; postoperative pain; mild-to-moderate pain due to inflammation and tissue injury; pyrexia; and renal colic. NSAIDs include salicylates, arlyalknoic acids, 2-arylpropionic acids (profens), N-arylanthranilic acids (fenamic acids), oxicams, coxibs (selective COX-2 inhibitors), sulphonanilides, diclofenac, diflunisal, etodolac, fenoprofen, flurbiprofen, ibuprofen, indomethacin, ketoprofen, ketorolac, mefenamic acid, meloxicam, nabumetone, naproxen, oxaprozin, piroxicam, salsalate, sulindac or tolmetin II. General The present invention provides engineered anti-TSLP antibodies and uses thereof to treat inflammatory, and particularly allergic inflammatory, disorders. In a preferred embodiment, the inflammatory disorder is asthma. In a preferred embodiment, the allergic inflammatory disorder is allergic rhinosinusitis, allergic asthma, allergic conjunctivitis, or atopic dermatitis. The present invention also provides engineered anti-TSLP antibodies to treat fibrosis, inflammatory bowel disease or Hodgkin's lymphoma.

As used herin, the term "TSLP" includes variants, isoforms, homologs, orthologs and paralogs of TSLP. The amino acid sequence of human TSLP is set forth in SEQ ID NO:4 of International Publication No. WO00/17362.

III. Engineered TSLP Specific Antibodies of the Invention

The invention relates to engineered anti-TSLP antibodies comprising specified CDR regions.

Methods for recombinantly engineering antibodies have been described, e.g., by Boss et al. (U.S. Pat. No. 4,816,397), Cabilly et al. (U.S. Pat. No. 4,816,567), Law et al. (European Patent Application Publication No. 438 310) and Winter (European Patent Application Publication No. 239400).

Engineered antibodies of the invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation can contain framework residues that differ from the germline sequence from which the antibody is derived. Such residues can be identified by comparing the antibody framework sequences to the germline sequences from which the antibody is derived.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043.

In addition or alternative to modifications made within the framework or CDR regions, antibodies of the invention can be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention can be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the antibody is an IgG4 isotype antibody comprising a Serine to Proline mutation at a position corresponding to position 228 (S228P; EU index) in the hinge region of the heavy chain constant region. This mutation has been reported to abolish the heterogeneity of inter-heavy chain disulfide bridges in the hinge region (Angal et al. supra; position 241 is based on the Kabat numbering system.

In one embodiment, the hinge region of CH1 is modified such that the number of cysteine residues in the hinge region is altered, e.g., increased or decreased. This approach is described further in U.S. Pat. No. 5,677,425. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745.

In another embodiment, the antibody is modified to increase its biological half life. Various approaches are possible. For example, one or more of the following mutations can be introduced: T252L, T254S, T256F, as described in U.S. Pat. No. 6,277,375. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022.

In yet other embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551.

In another example, one or more amino acid residues within amino acid positions 231 and 239 are altered to thereby alter the ability of the antibody to fix complement. This approach is described further in PCT Publication WO 94/29351.

In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072. Moreover, the binding sites on human IgG1 for FCγR1, FCγRII, FCγRIII and FcRn have been mapped and variants with improved binding have been described (see Shields et al. (2001) J. Biol. Chem. 276: 6591-6604). Specific mutations at positions 256, 290, 298, 333, 334 and 339 were shown to improve binding to FCγRIII. Additionally, the following combination mutants were shown to improve FCγRIII binding: T256A/S298A, S298A/E333A, S298A/K224A and S298A/E333A/K334A.

In still another embodiment, the glycosylation of an antibody is modified or altered, to delete or add carbohydrate moieties to the antibodies. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. See, e.g., U.S. Pat. Nos. 5,714,350 and 6,350,861.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, the cell lines Ms704, Ms705, and Ms709 lack the fucosyltransferase gene, FUT8 (α(1,6)-fucosyltransferase), such that antibodies expressed in the Ms704, Ms705, and Ms709 cell lines lack fucose on their carbohydrates. The Ms704, Ms705, and Ms709 FUT8−/− cell lines were created by the targeted disruption of the FUT8 gene in CHO/DG44 cells using two replacement vectors (see U.S. Patent Publication No. 20040110704 and Yamane-Ohnuki et al. (2004) *Biotechnol Bioeng* 87:614-22). As another example, EP 1,176,195 describes a cell line with a functionally disrupted FUT8 gene, which encodes a fucosyl transferase, such that antibodies expressed in such a cell line exhibit hypofucosylation by reducing or eliminating the α-1,6 bond-related enzyme. EP 1,176,195 also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 describes a variant CHO cell line, Lec13 cells, with reduced ability to attach fucose to Asn(297)-linked carbohydrates, also resulting in hypofucosylation of antibodies expressed in that host cell (see also Shields et al. (2002) *J. Biol. Chem.* 277:26733-26740). Antibodies with a modified glycosylation profile can also be produced in chicken eggs, as described in PCT Publication WO 06/089231. Alternatively, antibodies with a modified glycosylation profile can be produced in plant cells, such as Lemna. PCT Publication WO 99/54342 describes cell lines engineered to express glycoprotein-modifying glycosyl transferases (e.g., β(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) Nat. Biotech. 17:176-180). Alternatively, the fucose residues of the antibody can be cleaved off using a fucosidase enzyme; e.g., the fucosidase α-L-fucosidase removes fucosyl residues from antibodies (Tarentino et al. (1975) *Biochem.* 14:5516-23).

Another modification of the antibodies herein that is contemplated by this disclosure is pegylation. An antibody can be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See, e.g., EP 0 154 316 and EP 0 401 384.

Amino acid sequence variants of humanized anti-TSLP antibody of the invention can be prepared by introducing appropriate nucleotide changes into the humanized anti-TSLP antibody DNA, or by peptide synthesis. Such variants include, for example, deletions from, and/or insertions into and/or substitutions of, residues within the amino acid sequences shown for the humanized anti-TSLP antibodies disclosed and claimed herein. Any combination of deletion, insertion, and substitution can be made to arrive at the final construct, provided that the final construct possesses the desired characteristics. As discussed above, the amino acid changes also may alter post-translational processes of the humanized anti-TSLP antibody, such as changing the number or position of glycosylation sites.

A useful method for identification of certain residues or regions of the humanized anti-TSLP antibody polypeptide that are preferred locations for mutagenesis is called "alanine scanning mutagenesis," as described by Cunningham and Wells (1989) *Science* 244: 1081-1085. Here, a residue or group of target residues are identified (e.g., charged residues such as Arg, Asp, H is, Lys, and Glu) and replaced by a neutral or negatively charged amino acid (most preferably alanine or polyalanine) to affect the interaction of the amino acids with TSLP antigen. The amino acid residues demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, Ala scanning or random mutagenesis is conducted at the target codon or region and the expressed humanized anti-TSLP antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include humanized anti-TSLP antibody with an N-terminal methionyl residue or the antibody fused to an epitope tag. Other insertional variants of the humanized anti-TSLP antibody molecule include the fusion to the N- or C-terminus of humanized anti-TSLP antibody of an enzyme or a polypeptide which increases the serum half-life of the antibody.

Another type of variant is an amino acid substitution variant. These variants have at least one amino acid residue in the humanized anti-TSLP antibody molecule removed and a different residue inserted in its place. The sites of greatest interest for substitutional mutagenesis include the hypervariable loops, but FR alterations are also contemplated. Hypervariable region residues or FR residues involved in antigen binding are generally substituted in a relatively conservative manner.

Yet another type of amino acid variant is the substitution of residues to provide for greater chemical stability of the final humanized antibody.

In certain embodiments, it will be desirable to change certain amino acids containing exposed side-chains to another amino acid residue in order to provide for greater chemical stability of the final antibody, as follows. For example, an asparagine (Asn) residue may be changed to Gln or Ala to reduce the potential for formation of isoaspartate at any Asn-Gly sequences within a CDR. A similar problem may occur at a Asp-Gly sequence. Reissner and Aswad (2003) *Cell. Mol. Life. Sci.* 60:1281. Isoaspartate formation may debilitate or completely abrogate binding of an antibody to its target antigen. See, Presta (2005) *J. Allergy Clin. Immunol.* 116:731 at 734. In one embodiment, the asparagine is changed to glutamine (Gln). It may also be desirable to alter an amino acid adjacent to an asparagine (Asn) or glutamine (Gln) residue to reduce the likelihood of deamidation, which occurs at greater rates when small amino acids occur adjacent to asparagine or glutamine. See, Bischoff & Kolbe (1994) *J. Chromatog.* 662:261. In addition, any methionine residues (typically solvent exposed Met) in CDRs may be changed to Lys, Leu, Ala, or Phe in order to reduce the possibility that the methionine sulfur would oxidize, which could reduce antigen binding affinity and also contribute to molecular heterogeneity in the final antibody preparation. Id. In one embodiment, the methionine is changed to alanine (Ala). Additionally, in order to prevent or minimize potential scissile Asn-Pro peptide bonds, it may be desirable to alter any Asn-Pro combinations found in a CDR to Gln-Pro, Ala-Pro, or Asn-Ala. Antibodies with such substitutions are subsequently screened to ensure that the substitutions do not decrease TSLP binding affinity or other desired biological activity to unacceptable levels.

TABLE 2

Exemplary stabilizing CDR variants

| CDR Residue | Stabilizing Variant Sequence |
| --- | --- |
| Asn-Gly (N-G) | Gln-Gly, Ala-Gly, or Asn-Ala (Q-G), (A-G), or (N-A) |
| Asp-Gly (D-G) | Glu-Gly, Ala-Gly or Asp-Ala (E-G), (A-G), or (D-A) |
| Met (typically solvent exposed) (M) | Lys, Leu, Ala, or Phe (K), (L), (A), or (F) |
| Asn (N) | Gln or Ala (Q) or (A) |
| Asn-Pro (N-P) | Gln-Pro, Ala-Pro, or Asn-Ala (Q-P), (A-P), or (N-A) |

In addition, methionine residues in rodent CDRs may be changed to reduce the possibility that the methionine sulfur would oxidize, which could reduce antigen binding affinity and also contribute to molecular heterogeneity in the final antibody preparation. Id. In one embodiment, the methionine is changed to alanine (A). Antibodies with such substitutions are subsequently screened to ensure that the substitutions do not decrease TSLP binding affinity to unacceptable levels.

Nucleic acid molecules encoding amino acid sequence variants of humanized TSLP specific antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of humanized anti-TSLP antibody.

Ordinarily, amino acid sequence variants of the humanized anti-TSLP antibody will have an amino acid sequence having at least 97% amino acid sequence identity with the original humanized antibody amino acid sequences of either the heavy or the light chain more preferably at least 98%, more preferably at least 99%. Identity or homology with respect to this sequence is defined herein as the percentage of amino acid residues in the candidate sequence that are identical with the humanized anti-TSLP residues, after aligning the sequences and introducing gaps, if necessary, to achieve the maximum percent sequence identity, and not considering any conservative substitutions as part of the sequence identity. None of N-terminal, C-terminal, or internal extensions, deletions, or insertions into the antibody sequence shall be construed as affecting sequence identity or homology.

The humanized antibody can be selected from any class of immunoglobulins, including IgM, IgG, IgD, IgA, and IgE. Preferably, the antibody is an IgG antibody. Any isotype of IgG can be used, including $IgG_1$, $IgG_2$, $IgG_3$, and $IgG_4$. Variants of the IgG isotypes are also contemplated. The humanized antibody may comprise sequences from more than one class or isotype. Optimization of the necessary constant domain sequences to generate the desired biologic activity is readily achieved by screening the antibodies in the biological assays described below.

Likewise, either class of light chain can be used in the compositions and methods herein. Specifically, kappa, lambda, or variants thereof are useful in the present compositions and methods.

Any suitable portion of the CDR sequences from the non-human antibody can be used. The CDR sequences can be mutagenized by substitution, insertion or deletion of at least one residue such that the CDR sequence is distinct from the human and non-human antibody sequence employed. It is contemplated that such mutations would be minimal Typically, at least 95% of the humanized antibody residues will correspond to those of the non-human CDR residues, and most preferably greater than 97%.

Any suitable portion of the FR sequences from the human antibody can be used. The FR sequences can be mutagenized by substitution, insertion or deletion of at least one residue such that the FR sequence is distinct from the human and non-human antibody sequence employed. It is contemplated that such mutations would be minimal Typically, at least 75% of the humanized antibody residues will correspond to those of the human FR residues, more often 90%, and most preferably greater than 95%.

CDR and FR residues are determined according to the standard sequence definition of Kabat. Kabat et al., Sequences of Proteins of Immunological Interest, National Institutes of Health, Bethesda Md. (1987).

In a preferred embodiment, a binding composition according to the invention comprises, one or more of the following sequences:

The CDR-H1 sequence GYIFTDYAMH (SEQ ID NO: 1).
The CDR-H2 sequence TFIPLLDTSDYAQKFQG (SEQ ID NO: 2).
The CDR-H3 sequence MGVTHSYVMDA (SEQ ID NO: 3).
The CDR-L1 sequence RASQPISISVH (SEQ ID NO: 4).
The CDR-L2 sequence FASQSIS (SEQ ID NO: 5).
The CDR-L3 sequence QQTFSLPYT (SEQ ID NO: 6).
The variable heavy chain amino acid sequence shown in SEQ ID NO:7.
The variable light chain amino acid sequence shown in SEQ ID NO: 8.
The nucleic acid sequence encoding the variable heavy chain shown in SEQ ID NO:9.
The nucleic acid sequence encoding the variable light chain shown in SEQ ID NO:10.
The heavy chain amino acid sequence shown in SEQ ID NO:11. This sequence can further comprise the following leader sequence: MAVLGLLFCLVTFPSCVLS (SEQ ID NO:15).
The light chain amino acid sequence shown in SEQ ID NO: 12. This sequence can further comprise the following leader sequence: MAPVQLLGLLVLFLPAMRC (SEQ ID NO:16).
The nucleic acid sequence encoding the heavy chain is shown in SEQ ID NO:13. This sequence can further comprise a sequence encoding a leader sequence, preferably the following leader sequence: MAVLGLLF-CLVTFPSCVLS (SEQ ID NO:15).

The nucleic acid sequence encoding the light chain is shown in SEQ ID NO:14. This sequence can further comprise a sequence encoding a leader sequence, preferably the following leader sequence: MAPVQLLGLLVLFLPAMRC (SEQ ID NO:16).

For example, the present invention includes an isolated antibody or antigen-binding fragment thereof comprising a light chain immunoglobulin comprising CDR-L1, CDR-L2 and CDR-L3 (as set forth above) and a heavy chain immunoglobulin comprising CDR-H1, CDR-H2 and CDR-H3 (as set forth above). The present invention also includes an isolated antibody or antigen-binding fragment thereof comprising a light chain immunoglobulin variable region comprising the amino acid sequence set forth in SEQ ID NO: 8 or 12 and a heavy chain immunoglobulin variable region comprising the amino acid sequence set forth in SEQ ID NO: 7 and 11 (e.g., SEQ ID NO: 7 paired with SEQ ID NO: 8; or, SEQ ID NO: 11 paired with SEQ ID NO: 12). Such an antibody or fragment can, in an embodiment of the invention, be linked to an immunoglobulin constant domain such as IgG (e.g., $IgG_1$, $IgG_2$, $IgG_3$ or $IgG_4$). A pharmaceutical composition thereof, comprising said antibody or fragment and a pharmaceutically acceptable carrier, is also part of the present invention.

In some embodiments, different constant domains may be appended to the humanized $V_L$ and $V_H$ regions provided herein. For example, if a particular intended use of an antibody (or fragment) of the present invention were to call for altered effector functions, a heavy chain constant domain other than IgG1 may be used. Although IgG1 antibodies provide for long half-life and for effector functions, such as complement activation and antibody-dependent cellular cytotoxicity, such activities may not be desirable for all uses of the antibody. In such instances an IgG4 constant domain, for example, may be used.

IV. Antibody Conjugates

The binding compounds of the invention, for example the antibody or antibody fragments of the invention, may also be conjugated to a chemical moiety. The chemical moiety may be, inter alia, a polymer, a radionuclide or a cytotoxic factor. Preferably the chemical moiety is a polymer which increases the half-life of the antibody molecule in the body of a subject. Suitable polymers include, but are not limited to, polyethylene glycol (PEG) (e.g., PEG with a molecular weight of 2 kDa, 5 kDa, 10 kDa, 12 kDa, 20 kDa, 30 kDa or 40 kDa), dextran and monomethoxypolyethylene glycol (mPEG). Lee, et al., (1999) (*Bioconj. Chem.* 10:973-981) discloses PEG conjugated single-chain antibodies. Wen, et al., (2001) (*Bioconj. Chem.* 12:545-553) disclose conjugating antibodies with PEG which is attached to a radiometal chelator (diethylenetriaminpentaacetic acid (DTPA)).

The antibodies and antibody fragments of the invention may also be conjugated with labels such as $^{99}Tc$, $^{90}Y$, $^{111}In$, $^{32}P$, $^{14}C$, $^{125}I$, $^{3}H$, $^{131}I$, $^{11}C$, $^{15}O$, $^{13}N$, $^{18}F$, $^{35}S$, $^{51}Cr$, $^{57}To$, $^{226}Ra$, $^{60}Co$, $^{59}Fe$, $^{57}Se$, $^{152}Eu$, $^{67}Cu$, $^{217}Ci$, $^{211}At$, $^{212}Pb$, $^{47}Sc$, $^{109}Pd$, $^{234}Th$, and $^{40}K$, $^{157}Gd$, $^{55}Mn$, $^{52}Tr$ and $^{56}Fe$.

The antibodies and antibody fragments of the invention may also be conjugated with fluorescent or chemilluminescent labels, including fluorophores such as rare earth chelates, fluorescein and its derivatives, rhodamine and its derivatives, isothiocyanate, phycoerythrin, phycocyanin, allophycocyanin, o-phthaladehyde, fluorescamine, $^{152}Eu$, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels and stable free radicals.

The antibody molecules may also be conjugated to a cytotoxic factor such as diptheria toxin, *Pseudomonas aeruginosa* exotoxin A chain, ricin A chain, abrin A chain, modeccin A chain, alpha-sarcin, *Aleurites fordii* proteins and compounds (e.g., fatty acids), dianthin proteins, *Phytoiacca americana* proteins PAPI, PAPII, and PAP-S, *momordica charantia* inhibitor, curcin, crotin, *saponaria officinalis* inhibitor, mitogellin, restrictocin, phenomycin, and enomycin.

Any method known in the art for conjugating the antibody molecules of the invention to the various moieties may be employed, including those methods described by Hunter, et al., (1962) *Nature* 144:945; David, et al., (1974) *Biochemistry* 13:1014; Pain, et al., (1981) J. Immunol. Meth. 40:219; and Nygren, J., (1982) *Histochem. and Cytochem.* 30:407. Methods for conjugating antibodies are conventional and very well known in the art.

In yet other embodiments, different constant domains may be appended to humanized $V_L$ and $V_H$ regions derived from the CDRs provided herein. For example, if a particular intended use of an antibody (or fragment) of the present invention were to call for altered effector functions, a heavy chain constant domain other than IgG1 may be used, or hybrid IgG1/IgG4 may be utilized.

Although IgG1 antibodies provide for long half-life and for effector functions, such as complement activation and antibody-dependent cellular cytotoxicity, such activities may not be desirable for all uses of the antibody. In such instances an IgG4 constant domain, for example, may be used. In hu Mab8D5, the IgG4 constant domain differs from the native human IgG4 constant domain (Swiss-Prot Accession No. P01861.1, the disclosure of which is hereby incorporated by reference) at position 108, where the native Ser108 is replaced with Pro, in order to prevent a potential inter-chain disulfide bond between Cys106 and Cys109 that could interfere with proper intra-chain disulfide bond formation. See Angal et al. (1993) Mol. Immunol. 30:105.

V. Biological Activity of the Binding Compounds of the Invention

Binding compounds having the characteristics identified herein as being desirable in a humanized anti-TSLP antibody can be screened for inhibitory biologic activity in vitro or for suitable binding affinity.

Antibody affinities (e.g. for human TSLP) may be determined using standard analysis. Preferred humanized antibodies are those which bind human TSLP with a $K_D$ value of no more than about $1\times10^{-7}$ M; preferably no more than about $1\times10^{-8}$ M; more preferably no more than about $1\times10^{-9}$ M; and most preferably no more than about $1\times10^{-10}$ M.

The antibodies and fragments thereof useful in the present compositions and methods are biologically active antibodies and fragments. As used herein, the term "biologically active" refers to an antibody or antibody fragment that is capable of binding the desired the antigenic epitope and directly or indirectly exerting a biologic effect. Typically, these effects result from the failure of TSLP to bind its receptor. In one embodiment, the antibody and fragments thereof useful in the present compositions and methods inhibit: hTSLP induced proliferation of a Baf-3 cell line transfected with hTSLP-receptor and IL-7Ralpha; hTSLP induced luciferase expression from a Baf-3 cell line transfected with the TSLP-receptor and a luciferase reporter system; hTSLP induced TARC secretion from human primary monocytes isolated from PBMCs; and induction of Th2 differentiation.

As used herein, the term "specific" refers to the selective binding of the antibody to the target antigen epitope. Antibodies can be tested for specificity of binding by comparing binding to TSLP to binding to irrelevant antigen or antigen mixture under a given set of conditions. If the antibody binds to TSLP at least 10, and preferably 20 or 50 times more than to irrelevant antigen or antigen mixture then it is considered to be specific. An antibody that "specifically binds" to TSLP does not bind to proteins that do not comprise the TSLP-derived sequences, i.e. "specificity" as used herein relates to TSLP specificity, and not any other sequences that may be present in the protein in question. For example, as used herein, an antibody that "specifically binds" to TSLP will typically bind to FLAG-h TSLP, which is a fusion protein comprising TSLP and a FLAG® peptide tag, but it does not bind to the FLAG® peptide tag alone or when it is fused to a protein other than TSLP.

VI. Pharmaceutical Compositions

To prepare pharmaceutical or sterile compositions, the antibody or fragment thereof is admixed with a pharmaceutically acceptable carrier or excipient, see, e.g., *Remington's Pharmaceutical Sciences and U.S. Pharmacopeia: National Formulary*, Mack Publishing Company, Easton, Pa. (1984). Formulations of therapeutic and diagnostic agents may be prepared by mixing with physiologically acceptable carriers, excipients, or stabilizers in the form of, e.g., lyophilized powders, slurries, aqueous solutions or suspensions (see, e.g., Hardman, et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.).

Toxicity and therapeutic efficacy of the antibody compositions, administered alone or in combination with an immunosuppressive agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Antibodies exhibiting high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized.

Suitable routes of administration include parenteral administration, such as intramuscular, intravenous, or subcutaneous administration. Administration of antibody used in the pharmaceutical composition or to practice the method of the present invention can be carried out in a variety of conventional ways, such as oral ingestion, inhalation, topical application or cutaneous, subcutaneous, intraperitoneal, parenteral, intraarterial or intravenous injection. In one embodiment, the binding compound of the invention is administered intravenously. In another embodiment, the binding compound of the invention is administered subcutaneously.

Alternately, one may administer the antibody in a local rather than systemic manner, for example, via injection of the antibody directly into an arthritic joint or pathogen-induced lesion characterized by immunopathology, often in a depot or sustained release formulation. Furthermore, one may administer the antibody in a targeted drug delivery system, for example, in a liposome coated with a tissue-specific antibody, targeting, for example, arthritic joint or pathogen-induced lesion characterized by immunopathology. The liposomes will be targeted to and taken up selectively by the afflicted tissue.

Selecting an administration regimen for a therapeutic depends on several factors, including the serum or tissue turnover rate of the entity, the level of symptoms, the immunogenicity of the entity, and the accessibility of the target cells in the biological matrix. Preferably, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert, et al. (2003) *New Engl. J. Med.* 348: 601-608; Milgrom, et al. (1999) *New Engl. J. Med.* 341:1966-1973; Slamon, et al. (2001) *New Engl. J. Med.* 344:783-792; Beniaminovitz, et al. (2000) *New Engl. J. Med.* 342:613-619; Ghosh, et al. (2003) *New Engl. J. Med.* 348:24-32; Lipsky, et al. (2000) New *Engl. J. Med.* 343:1594-1602).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. Preferably, a biologic that will be used is derived from the same species as the animal targeted for treatment, thereby minimizing an inflammatory, autoimmune, or proliferative response to the reagent.

Antibodies, antibody fragments, and cytokines can be provided by continuous infusion, or by doses at intervals of, e.g., one day, one week, or 1-7 times per week. Doses may be provided intravenously, subcutaneously, topically, orally, nasally, rectally, intramuscular, intracerebrally, intraspinally, or by inhalation. A preferred dose protocol is one involving the maximal dose or dose frequency that avoids significant undesirable side effects. A total weekly dose is generally at least 0.05 ng/kg body weight, more generally at least 0.2 ng/kg, most generally at least 0.5 ng/kg, typically at least 1 ng/kg, more typically at least 10 ng/kg, most typically at least 100 ng/kg, preferably at least 0.2 mg/kg, more preferably at least 1.0 mg/kg, most preferably at least 2.0 mg/kg, optimally at least 10 mg/kg, more optimally at least 25 mg/kg, and most optimally at least 50 mg/kg (see, e.g., Yang, et al. (2003) *New Engl. J. Med.* 349:427-434; Herold, et al. (2002) *New Engl. J. Med.* 346:1692-1698; Liu, et al. (1999) *J. Neurol. Neurosurg. Psych.* 67:451-456; Portielji, et al. (20003) *Cancer Immunol. Immunother.* 52:133-144). The desired dose of a small molecule therapeutic, e.g., a peptide mimetic, natural product, or organic chemical, is about the same as for an antibody or polypeptide, on a moles/kg basis.

As used herein, "inhibit" or "treat" or "treatment" includes a postponement of development of the symptoms associated with autoimmune disease or pathogen-induced immunopathology and/or a reduction in the severity of such symptoms that will or are expected to develop. The terms further include ameliorating existing uncontrolled or unwanted autoimmune-related or pathogen-induced immunopathology symptoms, preventing additional symptoms, and ameliorating or preventing the underlying causes of such symptoms. Thus, the terms denote that a beneficial result has been conferred on a vertebrate subject with an inflammatory disease.

As used herein, the term "therapeutically effective amount" or "effective amount" refers to an amount of an anti-TSLP antibody or fragment thereof, that when administered alone or in combination with an additional therapeutic agent to a cell, tissue, or subject is effective to prevent or ameliorate the autoimmune disease or pathogen-induced immunopathology associated disease or condition or the progression of the disease. A therapeutically effective dose further refers to that amount of the compound sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. An effective amount of therapeutic will decrease the symptoms typically by at least 10%; usually by at least 20%; preferably at least about 30%; more preferably at least 40%, and most preferably by at least 50%.

Methods for co-administration or treatment with an anti-TSLP antibody or antigen-binding fragment thereof of the present invention and a second therapeutic agent, e.g., a cytokine, steroid, chemotherapeutic agent, antibiotic, or radiation (or any such agent discussed herein) form part of the present invention, see, generally, e.g., Hardman, et al. (eds.) (2001) *Goodman and Gilman's The Pharmacological Basis of Therapeutics*, 10th ed., McGraw-Hill, New York, N.Y.; Poole and Peterson (eds.) (2001) *Pharmacotherapeutics for Advanced Practice: A Practical Approach*, Lippincott, Williams & Wilkins, Phila., PA; Chabner and Longo (eds.) (2001) *Cancer Chemotherapy and Biotherapy*, Lippincott, Williams & Wilkins, Phila., PA. The antibodies and antigen-binding fragments thereof and pharmaceutical compositions thereof of the invention may also contain other immunosuppressive or immunomodulating agents. Any suitable immunosuppressive agent can be employed, including but not limited to anti-inflammatory agents, corticosteroids, cyclosporine, tacrolimus (i.e., FK-506), sirolimus, interferons, soluble cytokine receptors (e.g., sTNRF and sIL-1R), agents that neutralize cytokine activity (e.g., inflixmab, adalimumab, golimumab, etanercept), mycophenolate mofetil, 15-deoxyspergualin, thalidomide, glatiramer, azathioprine, leflunomide, cyclophosphamide, methotrexate, and the like. Non-steroidal anti-inflammatory drugs may also be provided with an antibody or antigen-binding fragment thereof or pharmaceutical composition thereof of the present invention. The pharmaceutical composition can also be employed with other therapeutic modalities such as phototherapy and radiation. The scope of the present invention includes compositions comprising any antibody or antigen-binding fragment thereof of the present invention and any second therapeutic agent (e.g., as discussed herein, e.g., wherein the antibody or fragment is formulated separately from the second therapeutic agent or wherein they are formulated together). Typical veterinary, experimental, or research subjects include monkeys, dogs, cats, rats, mice, rabbits, guinea pigs, horses, and humans.

VII. Antibody Production

For recombinant production of the antibodies of the present invention, the nucleic acids encoding the two chains are isolated and inserted into one or more replicable vectors for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence. In one embodiment, both the light and heavy chains of the humanized anti-TSLP antibody of the present invention are expressed from the same vector, e.g. a plasmid or an adenoviral vector.

Antibodies and antigen-binding fragments thereof of the present invention may be produced by any method known in the art. In one embodiment, antibodies are expressed in mammalian or insect cells in culture, such as Chinese hamster ovary (CHO) cells, human embryonic kidney (HEK) 293 cells, mouse myeloma NS0 cells, baby hamster kidney (BHK) cells, *Spodoptera frugiperda* ovarian (Sf9) cells. In one embodiment of the invention, the antibodies and antigen-binding fragments thereof are produced in fungal cells such as *Pichia* cells, *Pichia pastoris* cells, *Pichia finlandica* cells, *Pichia trehalophila* cells, *Pichia koclamae* cells, *Pichia membranaefaciens* cells, *Pichia minuta* cells (*Ogataea minuta, Pichia lindneri*), *Pichia opuntiae* cells, *Pichia thermotolerans* cells, *Pichia salictaria* cells, *Pichia guercuum* cells, *Pichia pijperi* cells, *Pichia stiptis* cells, *Pichia methanolica* cells, *Saccharomyces cerevisiae* cells, *Saccharomyces* cells, *Hansβnula polymorpha* cells, *Kluyveromyces* cells, *Kluyveromyces lactis* cells, *Candida albicans* cells, *Aspergillus nidulans* cells, *Aspergillus niger* cells, *Aspergillus oryzae* cells, *Trichoderma reesei* cells, *Chrysosporium lucknowense* cells, *Fusarium* cells, *Fusañum gramineum* cells, *Fusarium venenatum* cells or *Neuraspora crassa* cells.

In one embodiment, antibodies secreted from CHO cells are recovered and purified by standard chromatographic methods, such as protein A, cation exchange, anion exchange, hydrophobic interaction, and hydroxyapatite chromatography. Resulting antibodies are concentrated and stored in 20 mM sodium acetate, pH 5.5.

In another embodiment, the antibodies of the present invention are produced in yeast according to the methods described in WO2005/040395. Briefly, vectors encoding the individual light or heavy chains of an antibody of interest are introduced into different yeast haploid cells, e.g. different mating types of the yeast *Pichia pastoris*, which yeast haploid cells are optionally complementary auxotrophs. The transformed haploid yeast cells can then be mated or fused to give a diploid yeast cell capable of producing both the heavy and the light chains. The diploid strain is then able to secret the fully assembled and biologically active antibody. The relative expression levels of the two chains can be optimized, for example, by using vectors with different copy number, using transcriptional promoters of different strengths, or inducing expression from inducible promoters driving transcription of the genes encoding one or both chains.

In one embodiment, the respective heavy and light chains of the anti-TSLP antibody are introduced into yeast haploid cells to create a library of haploid yeast strains of one mating type expressing a plurality of light chains, and a library of haploid yeast strains of a different mating type expressing a plurality of heavy chains. These libraries of haploid strains can be mated (or fused as spheroplasts) to produce a series of diploid yeast cells expressing a combinatorial library of antibodies comprised of the various possible permutations of light and heavy chains. The combinatorial library of antibodies can then be screened to determine whether any of the antibodies has properties that are superior (e.g. higher affinity for TSLP) to those of the original antibodies. See. e.g., WO2005/040395.

In another embodiment, antibodies of the present invention are human domain antibodies in which portions of an antibody variable domain are linked in a polypeptide of molecular weight approximately 13 kDa. See, e.g., U.S. Pat. Publication No. 2004/0110941. Such single domain, low molecular weight agents provide numerous advantages in terms of ease of synthesis, stability, and route of administration.

VIII. Uses

The present invention provides methods for using engineered anti-TSLP for the treatment and diagnosis of inflammatory disorders (for example, in mammals such as humans).

In a preferred embodiment, the inflammatory disorder is asthma.

In another preferred embodiment, the inflammatory disorder is an allergic inflammatory disorder. In a preferred embodiment, the allergic inflammatory disorder is allergic rhinosinusitis, allergic asthma, allergic conjunctivitis, or atopic dermatitis.

The present invention provides methods for using engineered anti-TSLP for the treatment and diagnosis of fibrosis, inflammatory bowel disease, Hodgkin's lymphoma, respiratory viral infections or other viral infections, rheumatoid arthritis, or any other disorder characterized by inflammation at the site of injury.

The broad scope of this invention is best understood with reference to the following examples, which are not intended to limit the inventions to the specific embodiments.

All citations herein are incorporated herein by reference to the same extent as if each individual publication or patent application was specifically and individually indicated to be incorporated by reference.

Many modifications and variations of this invention can be made without departing from its spirit and scope, as will be apparent to those skilled in the art. The specific embodiments described herein are offered by way of example only, and the invention is to be limited by the terms of the appended claims, along with the full scope of equivalents to which such claims are entitled; and the invention is not to be limited by the specific embodiments that have been presented herein by way of example.

Example 1

General Methods

Standard methods in molecular biology are described (Maniatis et al. (1982) *Molecular Cloning, A Laboratory Manual*, Cold Spring Harbor Laboratory Press, Cold Spring Harbor, N.Y.; Sambrook and Russell (2001) *Molecular Cloning*, 3$^{rd}$ ed., Cold Spring Harbor Laboratory Press, Cold Spring Harbor, N.Y.; Wu (1993) *Recombinant DNA*, Vol. 217, Academic Press, San Diego, Calif.). Standard methods also appear in Ausbel et al. (2001) *Current Protocols in Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan et al. (2000) *Current Protocols in Protein Science, Vol. 1*, John Wiley and Sons, Inc., New York). Chemical analysis, chemical modification, post-translational modification, production of fusion proteins, glycosylation of proteins are described (see, e.g., Coligan et al. (2000) *Current Protocols in Protein Science, Vol. 2*, John Wiley and Sons, Inc., New York; Ausubel et al. (2001) *Current Protocols in Molecular Biology, Vol. 3*, John Wiley and Sons, Inc., NY, N.Y., pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies are described (Coligan et al. (2001) *Current Protcols in Immunology, Vol. 1*, John Wiley and Sons, Inc., New York; Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan et al. (2001) *Current Protcols in Immunology, Vol. 4*, John Wiley, Inc., New York).

Single chain antibodies and diabodies are described (see, e.g., Malecki et al. (2002) *Proc. Natl. Acad. Sci. USA* 99:213-218; Conrath et al. (2001) *J. Biol. Chem.* 276:7346-7350; Desmyter et al. (2001) *J. Biol. Chem.* 276:26285-26290; Hudson and Kortt (1999) *J. Immunol. Methods* 231:177-189; and U.S. Pat. No. 4,946,778). Bifunctional antibodies are provided (see, e.g., Mack, et al. (1995) *Proc. Natl. Acad. Sci. USA* 92:7021-7025; Carter (2001) *J. Immunol. Methods* 248: 7-15; Volkel, et al. (2001) *Protein Engineering* 14:815-823; Segal, et al. (2001) *J. Immunol. Methods* 248:1-6; Brennan, et al. (1985) *Science* 229:81-83; Raso, et al. (1997) *J. Biol. Chem.* 272:27623; Morrison (1985) *Science* 229:1202-1207; Traunecker, et al. (1991) *EMBO J.* 10:3655-3659; and U.S. Pat. Nos. 5,932,448, 5,532,210, and 6,129,914).

Bispecific antibodies are also provided (see, e.g., Azzoni et al. (1998) *J. Immunol.* 161:3493; Kita et al. (1999) *J. Immunol.* 162:6901; Merchant et al. (2000) *J. Biol. Chem.* 74:9115; Pandey et al. (2000) *J. Biol. Chem.* 275:38633; Zheng et al. (2001) *J. Biol. Chem.* 276:12999; Propst et al. (2000) *J. Immunol.* 165:2214; Long (1999) *Ann. Rev. Immunol.* 17:875).

Antibodies can be conjugated, e.g., to small drug molecules, enzymes, liposomes, polyethylene glycol (PEG). Antibodies are useful for therapeutic, diagnostic, kit or other purposes, and include antibodies coupled, e.g., to dyes, radioisotopes, enzymes, or metals, e.g., colloidal gold (see, e.g., Le Doussal et al. (1991) *J. Immunol.* 146:169-175; Gibellini et al. (1998) *J. Immunol.* 160:3891-3898; Hsing and Bishop (1999) *J. Immunol.* 162:2804-2811; Everts et al. (2002) *J. Immunol.* 168:883-889).

Methods for flow cytometry, including fluorescence activated cell sorting (FACS), are available (see, e.g., Owens et al. (1994) *Flow Cytometry Principles for Clinical Laboratory Practice*, John Wiley and Sons, Hoboken, N.J.; Givan (2001) *Flow Cytometry*, 2$^{nd}$ ed.; Wiley-Liss, Hoboken, N.J.; Shapiro (2003) *Practical Flow Cytometry*, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (Molecular Probes (2003) *Catalogue*, Molecular Probes, Inc., Eugene, Oreg.; Sigma-Aldrich (2003) *Catalogue*, St. Louis, Mo.).

Standard methods of histology of the immune system are described (see, e.g., Muller-Harmelink (ed.) (1986) *Human Thymus: Histopathology and Pathology*, Springer Verlag, New York, N.Y.; Hiatt, et al. (2000) *Color Atlas of Histology*, Lippincott, Williams, and Wilkins, Phila, Pa.; Louis, et al. (2002) *Basic Histology: Text and Atlas*, McGraw-Hill, New York, N.Y.).

Software packages and databases for determining, e.g., antigenic fragments, leader sequences, protein folding, functional domains, glycosylation sites, and sequence alignments, are available (see, e.g., GenBank, Vector NTI® Suite (Informax, Inc, Bethesda, Md.); GCG Wisconsin Package (Accelrys, Inc., San Diego, Calif.); DeCypher® (TimeLogic Corp., Crystal Bay, Nev.); Menne et al. (2000) *Bioinformatics* 16: 741-742; Menne et al. (2000) *Bioinformatics Applications Note* 16:741-742; Wren et al. (2002) *Comput. Methods Programs Biomed.* 68:177-181; von Heijne (1983) *Eur. J. Biochem.* 133:17-21; von Heijne (1986) *Nucleic Acids Res.* 14:4683-4690).

Example 2

Optimization of Anti-TSLP Antibody Sequence to Avoid Deamidation Problems

A humanized antibody that binds to human and cyno TSLP was disclosed in International Patent Publication WO2008/076321. Upon further analysis of this sequence, the inventor identified that the CDR-H2 of this antibody contains two asparagine (N) residues at positions 61 and 63 of SEQ ID NO: 4 of WO2008/076321 which could potentially deamidate and thereby disrupt the structure of the antibody potentially causing severe unintended problems affecting the safety and/or efficacy of the antibody. In order to avoid these problems, the inventors created an improved antibody that avoided these deamidation problems, yet preserved the affinity for human and cyno TSLP and avoided further problems relating to immunogenicity. This improved antibody comprises the variable heavy chain amino acid sequence of SEQ ID NO:7. The CDR-H2 of this amino acid sequence corresponds to SEQ ID NO:2.

FIG. 1 provides an alignment of SEQ ID NO:11 of the instant application against SEQ ID NO:14 of WO2008/076321 (i.e., an alignment of the heavy chains of the antibody claimed herein and the antibody disclosed in WO2008/076321. In FIG. 1, "Sequence 1" corresponds to SEQ ID NO:11 of the instant application and "Sequence 2" corresponds to ID NO:14 of WO2008/076321. In the antibody claimed herein, the asparagine (N) at position at position 61 of SEQ ID NO: 14 of WO2008/076321 was changed to alanine (A) and the asparagine at position 63 of SEQ ID NO: 14 was changed to lysine (K). These changes were made to avoid the potential deamidation of these residues. Additionally, the lysine (K) at position 65 of SEQ ID NO: 4 of WO2008/076321 was changed to Glutamine (Q). This change was made to decrease the chances of creating immunogenicity. A further change was made at position 72 of SEQ ID NO: 14 of WO2008/076321, where a threonine (T) was changed to an alanine (A). This change was made to improve the binding affinity of the antibody.

It was surprisingly found that the changes in CDR-H2 did not substantially affect the binding affinity of the resulting antibody.

A vector containing the genes encoding the heavy and light chain of the antibody disclosed herein was deposited with the ATCC, 10801 University Blvd., Manassas, Va. 20110-2209, on Nov. 17, 2009 and received ATCC Deposit No. PTA-10482. This deposit was made under the conditions provided by the Budapest Treaty. The nucleic acid sequences encoding the light and heavy chains (including signal peptides) are in a single plasmid, and both genes are expressed from the human cytomegalovirus (CMV) promoter. The plasmid also contains an ampicillin resistant gene for selection in mammalian cells and a DHFR gene for gene amplification.

Example 3

Determining the Equilibrium Dissociation Constant ($K_D$) for Humanized Anti-human TSLP Using KinExA Technology The equilibrium dissociation constant ($K_D$) was determined using the KinExA 3000 instrument (Sapidyne Instruments Inc., www.sapidyne.com). The KinExA uses the principle of the Kinetic Exclusion Assay method based on measuring the concentration of uncomplexed antibody in a mixture of antibody, antigen and antibody-antigen complex. The concentration of free antibody is measured by exposing the mixture to a solid-phase immobilized antigen for a very brief period of time. In practice, this is accomplished by flowing the solution phase antigen-antibody mixture past antigen-coated particles trapped in a flow cell. Data generated by the instrument are analyzed using custom software. Equilibrium constants are calculated using a mathematical theory based on the following assumptions:

1. The binding follows the reversible binding equation for equilibrium:

$$k_{on}[Ab][Ag]=k_{off}[AbAg]$$

2. Antibody and antigen bind 1:1 and total antibody equals antigen-antibody complex plus free antibody.

3. Instrument signal is linearly related to free antibody concentration.

Materials

Antibodies:
  Antibody 1: Parental rat antibody 23B12
  Antibody 2: Humanized anti hu TSLP mAb 23B12 (comprising the heavy chain of SEQ ID NO:14 and the light chain of SEQ ID NO:16 of WO2008/076321)
  Antibody 3: Humanized anti hu TSLP mAb 23B12 (comprising the heavy chain of SEQ ID NO:14 with a mutation at position 72 from T to A, and the light chain of SEQ ID NO:16 of WO2008/076321
  Antibody 4: Humanized anti hu TSLP mAb 23B12 (comprising the heavy chain of SEQ ID NO:11 and the light chain of SEQ ID NO:12 of the instant application)

Antigens:
  Recombinant human TSLP

Biotinylated antigens:
  Biotinylated human TSLP

Other reagents:
  PMMA particles, 98 micron (Sapidyne, Cat No. 440198)
  Neutravidin (Pierce, Cat No. 31000)
  Cy5-conjugated Goat anti-rat IgG (H+L) (Jackson Immunoresearch Laboratories Cat. No 112-175-167, Lot 60306)
  Cy5-conjugated Goat anti-HuIgG (H+L) (Jackson Immunoresearch Laboratories Cat. No 109-175-088, lot 49069 and lot 58552)

Experimental Conditions:
  PMMA particles were coated with biotinylated human TSLP according to Sapidyne "Protocol for coating PMMA particles with biotinylated ligands having short or nonexistent linker arms". All experimental procedures were done according to the KinExA 3000 manual. All runs were done in duplicate.

The following conditions were used:
Sample volume: 2 mL
Sample flow rate: 0.25 mL/min
Label volume: 1 mL
Label flow rate: 0.25 mL/min
Antibody conc.: 0.1 nM Highest antigen conc.: 10 nM
Lowest antigen conc.: 10 μM Two-fold serial dilutions of the antigen were prepared and mixed with the antibody at constant concentration. The mixture was incubated for 2 hours at 25° C. to equilibrate.

TABLE 3

$K_D$ Values Determined by KinExa

| mAb | TSLP | Expression | $K_D$ (pM) |
|---|---|---|---|
| Antibody 1 | human | HEK293 | 1.1 |
| Antibody 2 | human | HEK293 | 7.7 |
| Antibody 3 | human | HEK293 | 1.6 |
| Antibody 4 | human | HEK293 | 3.2 |

Example 4

Affinity of Antibodies for Human and Cyno TSLP

The kinetic binding activities of the parental rat and the various humanized derivative anti human TSLP antibodies against both human (hu) and cynomolgus monkey (cyno) TSLP were measured by surface plasmon resonance using a BIAcore T100 system (BIAcore AB, Upsalla, Sweden). Approximately 100RUs of human TSLP or cyno TSLP were immobilized via amine coupling chemistry onto a Sensor Chip CM5 (Research grade, BR-1006-68). HBS-EP buffer (BR-1006-69) was used as the running buffer with a flow rate of 30 μL/min. rat and humanized 23B12 antibodies at varying concentrations ranging from 0.82 to 600 nM were injected over the immobilized hu or cyno TSLP surfaces at a flow rate of 30 μL/min. Following each injection cycle the CM5 chip surface was regenerated using a series of solutions (10 mM Glycine pH 1.5 and 25 mM NaOH repectively) at a flow rate of 75 μL/min.

Background subtraction binding sensorgrams were used for analyzing the rate constant of association (ka) and dissociation (kd), and the equilibrium dissociation constant $K_D$. The resulting data sets were fitted with a bivalent analyte model using the BIAevaluation software (version 1.0). The $K_D$ determined for the various antibodies are shown in Table 4. The results of individual experiments are shown in separate lines.

TABLE 4

BIAcore Analysis

| TSLP | KD (pM) | | | |
|---|---|---|---|---|
| | Antibody 1 | Antibody 2 | Antibody 3 | Antibody 4 |
| human | 141 | Not determined | Not determined | 172 |
| human | 130 | 150 | 128 | Not determined |
| human | Not determined | Not determined | Not determined | 155, 142, 339, 170, 153 |
| human* | Not determined | Not determined | Not determined | 339 |
| human*,** | Not determined | Not determined | Not determined | 299 |
| cyno | 159 | Not determined | Not determined | 138, 80, 115 |
| cyno | Not determined | Not determined | Not determined | 127 |
| cyno** | Not determined | Not determined | Not determined | 381 |

*This particular experiment used TSLP purchased from R&D and expressed in E. coli. The other experiments were conducted with TSLP expressed in HEK293 cells.
**These experiments were conducted at 37° C. All other experiments were conducted at room temperature.
Antibody 1: Parental rat antibody 23B12
Antibody 2: Humanized anti hu TSLP mAb 23B12 (comprising the heavy chain of SEQ ID NO: 14 and the light chain of SEQ ID NO: 16 of WO2008/076321)
Antibody 3: Humanized anti hu TSLP mAb 23B12 (comprising the heavy chain of SEQ ID NO: 14 with a mutation at position 72 from T to A; and the light chain of SEQ ID NO: 16 of WO2008/076321)
Antibody 4: Humanized anti hu TSLP mAb 23B12 (comprising the heavy chain of SEQ ID NO: 11 and the light chain of SEQ ID NO: 12 of the instant application)

Example 5

Proliferation Bioassay for the Assessment of Neutralizing Anti-TSLP Antibody

The ability of the various anti-TSLP antibodies to biologically neutralize human and cyno TSLP was assessed by the application of short-term proliferation bioassays that utilize cells which express recombinant human and cyno TSLP receptors. The transfectant Ba/F3-TSLPR-IL7Ra cells proliferate in response to TSLP and the response can be inhibited by a neutralizing anti-TSLP antibody. Each antibody was titrated against a concentration of TSLP chosen within the linear region of the TSLP dose-response curve, near plateau and above the TSLP $EC_{50}$. Proliferation, or lack thereof, is measured by colorimetric means using Alamar Blue, a growth indicator dye based on detection of metabolic activity. The ability of an antibody to neutralize TSLP is assessed by its EC50 value, or concentration of antibody that induces half-maximal inhibition of TSLP proliferation.

Ba/F3 transfectants are maintained in RPMI-1640 medium, 10% fetal calf serum, 50 μM 2-mercaptoethanol, 2 mM L-Glutamine, 50 μg/mL penicillin-streptomycin, and 10 ng/mL mouse IL-3.

Ba/F3 proliferation bioassays are performed in RPMI-1640 medium, 10% fetal calf serum, 50 μM 2-mercaptoethanol, 2 mM L-Glutamine, and 50 μg/mL penicillin-streptomycin.

The assay is performed in 96-well flat bottom plates (Falcon 3072 or similar). All preparations of reagents and cell suspensions utilize the appropriate bioassay medium. The assay volume is 150 μL per well. Titrations of an anti-TSLP antibody are pre-incubated with TSLP for 30-60 minutes at room temperature, during which time cells are prepared. Cells are added to plates following the antibody-cytokine pre-incubation. Bioassay plates are incubated in a humidified tissue culture chamber (37C, 5% $CO_2$) for 40-48 hours. At the end of the culture time, Alamar Blue (Biosource Cat #DAL1100) is added and allowed to develop for 8-12 hours. Absorbance is then read at 570 nm and 600 nm (VERSAmax Microplate Reader, Molecular Probes), and an $OD_{570-600}$ is obtained. Duplicates or triplicates are recommended.

Cells are used in a healthy growth state, generally at densities of $3-8 \times 10^5$/mL. Cells are counted, pelleted, washed twice in bioassay medium, and suspended to the appropriate density for plating.

TSLP was prepared to working concentration and added to first well at 75 μL. Serial dilutions of 1:3 were made by titrating 25:50 μL in bioassay medium across wells, leaving 50 μL/well. Cells were suspended to the appropriate density for plating at 100 μL per well.

The antibody was prepared to working concentration and added to the first well at 75 μL. Serial dilutions of 1:3 were made by titrating 25:50 μL in bioassay medium across wells, leaving 50 μL per well. TSLP at the appropriate concentration was added at 50 μL per well to the wells containing the titrated antibody. Cells were suspended to the appropriate density for plating at 50 μL per well, and added following the antibody-cytokine pre-incubation.

Using GraphPad Prism 3.0 software, absorbance was plotted against cytokine or antibody concentration and EC50 values were determined using non-linear regression (curve fit) of sigmoidal dose-response.

The assay results are shown in Table 5. The results of individual experiments are shown in separate lines.

TABLE 5

Inhibition Of Proliferation

EC 50 (μg/ml)

| TSLP | Antibody 1 | Antibody 2 | Antibody 3 | Antibody 4 |
|---|---|---|---|---|
| human | 0.022 | Not determined | Not determined | 0.041 |
| human | 0.025 | 0.092 | 0.054 | Not determined |
| human | 0.014 | Not determined | Not determined | 0.024 |
| human* | 0.083 | Not determined | Not determined | 0.215, 0.137 |
| cyno | 0.064 | Not determined | Not determined | 0.117, 0.077 |
| cyno | 0.122 | Not determined | Not determined | 0.158 |
| cyno | 0.054 | Not determined | Not determined | 0.067 |

*This particular experiment used TSLP purchased from R&D and expressed in E. coli. The other experiments were conducted with TSLP expressed in HEK293 cells.
Antibody 1: Parental rat antibody 23B12
Antibody 2: Humanized anti hu TSLP mAb 23B12 (comprising the heavy chain of SEQ ID NO: 14 and the light chain of SEQ ID NO: 16 of WO2008/076321)
Antibody 3: Humanized anti hu TSLP mAb 23B12 (comprising the heavy chain of SEQ ID NO: 14 with a mutation at position 72 from T to A; and the light chain of SEQ ID NO: 16 of WO2008/076321)
Antibody 4: Humanized anti hu TSLP mAb 23B12 (comprising the heavy chain of SEQ ID NO: 11 and the light chain of SEQ ID NO: 12 of the instant application)

A summary of the results presented in Table 5 including average values and SD (standard deviation) is provided in Table 6. (Only the values obtained using TSLP expressed in HEK293 cells were used to calculate the values provided in Table 6.)

TABLE 6

| | Bioassay (pM) Ba/F3 transfectant | |
|---|---|---|
| | hTSLP (SD) | cTSLP (SD) |
| Antibody 1 | 120 (37) | 528 (242) |
| Antibody 4 | 214 (80) | 691 (274) |

Example 6

Neutralizing Activity Of Anti-TSLP On TSLP Induced TARC Production By Human Primary Dendritic Cells Peripheral blood mononuclear cells (PBMCs) were isolated from buffy coats obtained from healthy blood donors (Stanford Medical School Blood Center, Stanford, Calif.) by Ficoll centrifugation and CD11c+ Dendritic Cells were obtained by MACS (Miltenyi Biotech, Auburn, Calif.) using negative selection followed by cell sorting using a FACS. Lineage negative (Lin⁻) cells were obtained by MACS depletion of T cells, B cells, NK cells, red blood cells and monocytes form PBMC using mouse anti-human CD3 mAb (OKT3, DNAX) and mouse anti-CD16 mAb and goat anti-mouse IgG coated magnetic beads (Miltenyi Biotech), and using magnetic beads directly coated with anti-CD19, CD56 and CD14 mAbs (Miltenyi Biotech). Subsequently, Lin⁻ cells were stained with TC-anti-CD4 (Caltag, Burlingame, Calif.), PE-anti-CD11c and FITC-anti-CD3, -CD14, -CD19, -CD56, -CD16, and -CD20 (all BD Biosciences, San Diego, Calif.) and CD11c+ DC sorted on a Vantage FACsorter™ (BD Biosciences) to a purity>99% of CD11c⁺ CD4⁺ Lin⁻ cells.

CD11c⁺ CD4⁺ DCs were cultured immediately after sorting in RPMI (Mediatech, Herndon, Va.) containing 10% FCS and 1% pyruvate (Mediatech), HEPES (Invitrogen, Grand Island, N.Y.) and penicillin-streptomycin (Mediatech). Cells were seeded at $0.5 \times 10^6$/ml in flat-bottomed 96-well plates in the presence of medium alone, TSLP (15 ng/ml, DNAX), or in a combination of TSLP and the neutralizing anti-TSLP mAb (clone 23B12) or an anti-TSLPR monoclonal antibody or an isotype control rat IgG2a (R&D Systems, Minneapolis, Minn.). DC culture supernatants were collected after 24 h of culture, stored frozen at −20° C. and analyzed for TARC protein levels by ELISA (R&D Systems).

The results are summarized in Table 7. The results of individual experiments are shown in separate lines.

TABLE 7

| | EC 50 (μg/ml) | |
|---|---|---|
| TSLP | Antibody 1 | Antibody 4 |
| human | 0.12 | 0.16 |
| human | 0.0069 | 0.0077 |
| human | 0.031 | 0.060 |
| human (R&D)* | 0.050 | 0.102, 0.126 |
| human (R&D)* | 0.113 | 0.067, 0.173 |
| human (R&D)* | 0.228 | 0.424 |
| human (R&D)* | 0.404 | 0.164 |

*These experiments used TSLP purchased from R&D and expressed in E. coli. The other experiments were conducted with TSLP expressed in HEK293 cells.
Antibody 1: Parental rat antibody 23B12
Antibody 4: Humanized anti hu TSLP mAb 23B12 (comprising the heavy chain of SEQ ID NO: 11 and the light chain of SEQ ID NO: 12 of the instant application)

A summary of the results presented in Table 7 including average values and SD (standard deviation) is provided in Table 8.

TABLE 8

| | Bioassay (pM) TARC production by human DCs | |
|---|---|---|
| | hTSLP (SD) | hTSLP* (SD) |
| Antibody 1 | 345 (389) | 1312 (1025) |
| Antibody 4 | 492 (502) | 1161 (843) |

*These experiments used TSLP purchased from R&D and expressed in E. coli. The other experiments were conducted with TSLP expressed in HEK293 cells.

Example 7

Neutralizing Activity Of Anti-TSLP Antibodies On TSLP-Induced MDC Production By Cynomolgus Monkey Splenocytes Total splenocyte suspensions were prepared from Cynomolgus monkey spleen by disruption of the tissue and passing it through a 50 mesh stainless steel tissue sieve (Bellco) followed by passage through a 70 micrometer Nylon Cell strainer (BD Falcon). Cell suspensions were washed in DPBS by centrifugation and cell pellets were resuspended in prewarmed 37° C. ACK lysis Buffer (BioWhittaker) to lyse Red Blood Cells and incubated for 5 minutes at 37° C. Cells were diluted in DPBS, washed twice and resuspended in culture medium.

Splenocytes were cultured in RPMI (Mediatech, Herndon, Va.) containing 10% FCS and 1% pyruvate (Mediatech), HEPES (Invitrogen, Grand Island, N.Y.) and penicillin-streptomycin (Mediatech). Cells were seeded at $1.0 \times 10^6$/ml in flat-bottomed 96-well plates in the presence of medium alone, TSLP (0.1 ng/ml), or in a combination of TSLP and the neutralizing anti-TSLP mAb (Antibody 1 or Antibody 4). Splenocyte culture supernatants were collected after 120 h of culture, stored frozen at −20° C. and analyzed for MDC protein levels by a human MDC ELISA (R&D Systems).

The results are summarized in Table 9. The results of individual experiments are shown in separate lines.

TABLE 9

| | IC 50 (ug/ml) | |
|---|---|---|
| TSLP | Antibody 1 | Antibody 4 |
| cyno | 0.012 | 0.012 |
| cyno | 0.030 | 0.028, 0.008 |
| cyno | 0.018 | 0.054 |
| cyno | 0.033 | 0.023 |

Antibody 1: Parental rat antibody 23B12
Antibody 4: Humanized anti hu TSLP mAb 23B12 (comprising the heavy chain of SEQ ID NO: 11 and the light chain of SEQ ID NO: 12 of the instant application)

Many modifications and variations of this invention can be made without departing from its spirit and scope, as will be apparent to those skilled in the art. The specific embodiments described herein are offered by way of example only, and the invention is to be limited by the terms of the appended claims, along with the full scope of equivalents to which such claims are entitled; and the invention is not to be limited by the specific embodiments that have been presented herein by way of example.

Citation of the above publications or documents is not intended as an admission that any of the foregoing is pertinent prior art, nor does it constitute any admission as to the contents or date of these publications or documents. U.S. patents and other publications referenced herein are hereby incorporated by reference.

SEQUENCE LISTING

The present invention includes any isolated polypeptide or isolated nucleic acid including any of the following amino acid or nucleotide sequences, respectively:

| SEQ ID NO: | Sequence |
|---|---|
| 1 | GYIFTDYAMH |
| 2 | TFIPLLDTSDYAQKFQG |
| 3 | MGVTHSYVMDA |
| 4 | RASQPISISVH |
| 5 | FASQSIS |
| 6 | QQTFSLPYT |
| 7 | variable heavy chain amino acid sequence<br>QVQLVQSGAEVKKPGASVKVSCKASGYIFTDYAMHWVRQAPGQGLEWMGTFIPLLDTSDYAQK<br>FQGRVTMTADTSTSTAYMELRSLRSDDTAVYYCARMGVTHSYVMDAWGQGTLVTVSS |
| 8 | variable light chain amino acid sequence<br>EIVLTQSPGTLSLSPGERATLSCRASQPISISVHWYQQKPGQAPRLLIYFASQSISGIPDRFSGSG<br>SGTDFTLTISRLEPEDFAVYYCQQTFSLPYTFGQGTKVEIKRT |
| 9 | nucleic acid sequence encoding variable heavy chain<br>caggtgcagctggtgcagtctggcgccgaagtgaagaaacctggcgcctccgtgaaggtgtcctgcaaggcctccggctacatcttca<br>ccgactacgccatgcactgggtccgccaggctccaggacagggcctggaatggatgggcaccttcatccctctgctggacacctctga<br>ctacgcccagaaattccagggcagagtgaccatgaccgccgacacctccacctccaccgcctacatggaactgcggtccctgagatc<br>cgacgacaccgccgtgtactactgcgcccggatgggcgtgacacactcctacgtgatggacgcttggggccagggcaccctggtcac<br>cgtgtcctcc |
| 10 | nucleic acid sequence encoding the variable light chain<br>gagatcgtgctgacccagtccctggcaccctgtctctgtctcccggcgagagagccaccctgtcctgccgggcctcccagcctatctcc<br>atctccgtgcactggtatcagcagaagccaggacaggcccctcggctgctgatctacttcgcttctcagtctatctctggcatccctgaccg |

-continued

```
gttctccggctctggctccggcaccgacttcaccctgaccatctcccggctggaacctgaggacttcgccgtgtactactgccagcagac
cttctccctgccttacaccttcggccagggcaccaaggtggagatcaagcgtacg
```

11 heavy chain amino acid sequence
QVQLVQSGAEVKKPGASVKVSCKASGYIFTDYAMHWVRQAPGQGLEWMGTFIPLLDTSDYAQK
FQGRVTMTADTSTSTAYMELRSLRSDDTAVYYCARMGVTHSYVMDAWGQGTLVTVSSASTKG
PSVFPLAPSSKSTSGGTAALGCLVKDYFPEPVTVSWNSGALTSGVHTFPAVLQSSGLYSLSSVV
TVPSSSLGTQTYICNVNHKPSNTKVDKKVEPKSCDKTHTCPPCPAPELLGGPSVFLFPPKPKDTL
MISRTPEVTCVVVDVSHEDPEVKFNWYVDGVEVHNAKTKPREEQYNSTYRVVSVLTVLHQDWL
NGKEYKCKVSNKALPAPIEKTISKAKGQPREPQVYTLPPSRDELTKNQVSLTCLVKGFYPSDIAVE
WESNGQPENNYKTTPPVLDSDGSFFLYSKLTVDKSRWQQGNVFSCSVMHEALHNHYTQKSLSL
SPGK 12 light chain amino acid sequence
EIVLTQSPGTLSLSPGERATLSCRASQPISISVHWYQQKPGQAPRLLIYFASQSISGIPDRFSGSG
SGTDFTLTISRLEPEDFAVYYCQQTFSLPYTFGQGTKVEIKRTVAAPSVFIFPPSDEQLKSGTASV
VCLLNNFYPREAKVQWKVDNALQSGNSQESVTEQDSKDSTYSLSSTLTLSKADYEKHKVYACE
VTHQGLSSPVTKSFNRGEC 13 nucleic acid sequence encoding the heavy chain
```
caggtgcagctggtgcagtctggcgccgaagtgaagaaacctggcgcctccgtgaaggtgtcctgcaaggcctccggctacatcttca
ccgactacgccatgcactgggtccgccaggctccaggacagggcctggaatggatgggcaccttcatcctctgctggacacctctga
ctacgcccagaaattccagggcagagtgaccatgaccgccgacacctccacctccaccgcctacatggaactgcggtccctgagatc
cgacgacaccgccgtgtactactgcgcccggatgggcgtgacacactcctacgtgatggacgcttggggccagggcaccctggtcac
cgtgtcctccgctagcaccaaggcccttccggtgttccctcctggccccttcctccaagtctacctctggcggcaccgctgctctgggctgtct
ggtcaaggactacttccctgagcgtgacagtctcttggaactctggccctgacctccggcgtgcacaccttcctgccgtgctgcagt
ctagtggcctgtactccctgtcctccgtggtcacagtgccttcatcatccctgggcacccagacctatctgcaacgtgaaccacaagcc
ttccaacaccaaggtggacaagaaggtggagcctaagtcctgcgacaagacccacacctgtcctccatgccctgcccctgagctgctg
ggcggacccctccgtgttcctgttccctcctaagcctaaggacaccctgatgatctcccggaccccctgaagtgacctgcgtggtggtggac
gtgtcccacgaggacccagaagtgaagttcaattggtacgtggacggcgtggaggtgcacaacgccaagaccaagcctcgggagg
aacagtacaactccacctaccgggtggtgtccgtgctgaccgtgctgcaccaggactggctgaacggcaaagaatacaagtgcaagg
tgtccaacaaggccctgcctgcccctatcgaaaagaccatctccaaggccaagggccagccaagagaacctcaggtgtacaccctg
cctccctctcgggacgagctgaccaagaaccaggtgtccctgacatgcctggtcaagggcttctacccttccgatatcgccgtggagtgg
gagtctaacggccagcctgagaacaactacaagaccaccccctcctgtgctggactccgacggctccttcttcctgtactccaagctgacc
gtggacaagtcccggtggcagcagggcaacgtgttctcctgctccgtgatgcacgaggccctgcacaaccactacacccagaagtcc
ctgtccctgtctcctggcaag 14 nucleic acid sequence encoding the light chain
gagatcgtgctgacccagtcccctggcaccctgtctctgtctcccggcgagagagccaccctgtcctgccgggcctccagcctatctcc
atctccgtgcactggtatcagcagaagccaggacaggcccctcggctgctgatctacttcgcttctcagtctatctctggcatccctgaccg
gttctccggctctggctccggcaccgacttcaccctgaccatctcccggctggaacctgaggacttcgccgtgtactactgccagcagac
cttctccctgccttacaccttcggccagggcaccaaggtggagatcaagcgtacggtggccgctcctccgtgttcatcttccctccctccg
acgagcagctgaagtccggcaccgcctctgtcgtcctgctgctgaacaacttctaccctcgggaggccaaggtgcagtggaaggtgga
caacgccctgcagtccggcaactcccaggaatccgtcaccgagcaggactccaaggactctacctactcctgtcctccaccctgacc
ctgtccaaggccgactacgagaagcacaaggtgtacgcctgcgaagtgacccaccagggcctgtcatctccagtgactaagtctttca
accggggcgagtgc

15 MAVLGLLFCLVTFPSCVLS

16 MAPVQLLGLLVLFLPAMRC

SEQUENCE LISTING

<160> NUMBER OF SEQ ID NOS: 16

<210> SEQ ID NO 1
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Gly Tyr Ile Phe Thr Asp Tyr Ala Met His
1               5                   10

<210> SEQ ID NO 2
<211> LENGTH: 17
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic peptide"

<400> SEQUENCE: 2

Thr Phe Ile Pro Leu Leu Asp Thr Ser Asp Tyr Ala Gln Lys Phe Gln
1               5                   10                  15

Gly

<210> SEQ ID NO 3
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Met Gly Val Thr His Ser Tyr Val Met Asp Ala
1               5                   10

<210> SEQ ID NO 4
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Arg Ala Ser Gln Pro Ile Ser Ile Ser Val His
1               5                   10

<210> SEQ ID NO 5
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Phe Ala Ser Gln Ser Ile Ser
1               5

<210> SEQ ID NO 6
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gln Gln Thr Phe Ser Leu Pro Tyr Thr
1               5

<210> SEQ ID NO 7
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asp Tyr
            20                  25                  30

Ala Met His Trp Val Arg Gln Ala Pro Gly Gln Gly Leu Glu Trp Met
        35                  40                  45

Gly Thr Phe Ile Pro Leu Leu Asp Thr Ser Asp Tyr Ala Gln Lys Phe
    50                  55                  60

Gln Gly Arg Val Thr Met Thr Ala Asp Thr Ser Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Met Gly Val Thr His Ser Tyr Val Met Asp Ala Trp Gly Gln
            100                 105                 110

Gly Thr Leu Val Thr Val Ser Ser
        115                 120

<210> SEQ ID NO 8
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Pro Ile Ser Ile Ser
            20                  25                  30

Val His Trp Tyr Gln Gln Lys Pro Gly Gln Ala Pro Arg Leu Leu Ile
        35                  40                  45

Tyr Phe Ala Ser Gln Ser Ile Ser Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Thr Phe Ser Leu Pro Tyr
                85                  90                  95

Thr Phe Gly Gln Gly Thr Lys Val Glu Ile Lys Arg Thr
            100                 105

<210> SEQ ID NO 9
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 9
caggtgcagc tggtgcagtc tggcgccgaa gtgaagaaac ctggcgcctc cgtgaaggtg      60
tcctgcaagg cctccggcta catcttcacc gactacgcca tgcactgggt ccgccaggct     120
ccaggacagg gcctggaatg gatgggcacc ttcatccctc tgctggacac ctctgactac     180
gcccagaaat tccagggcag agtgaccatg accgccgaca cctccaccte caccgcctac     240

```
atggaactgc ggtccctgag atccgacgac accgccgtgt actactgcgc ccggatgggc      300
gtgacacact cctacgtgat ggacgcttgg ggccagggca ccctggtcac cgtgtcctcc      360
```

<210> SEQ ID NO 10
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 10

```
gagatcgtgc tgacccagtc ccctggcacc ctgtctctgt ctcccggcga gagagccacc       60
ctgtcctgcc gggcctccca gcctatctcc atctccgtgc actggtatca gcagaagcca      120
ggacaggccc ctcggctgct gatctacttc gcttctcagt ctatctctgg catccctgac      180
cggttctccg gctctggctc cggcaccgac ttcaccctga ccatctcccg gctggaacct      240
gaggacttcg ccgtgtacta ctgccagcag accttctccc tgccttacac cttcggccag      300
ggcaccaagg tggagatcaa gcgtacg                                          327
```

<210> SEQ ID NO 11
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 11

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asp Tyr
            20                  25                  30

Ala Met His Trp Val Arg Gln Ala Pro Gly Gln Gly Leu Glu Trp Met
        35                  40                  45

Gly Thr Phe Ile Pro Leu Leu Asp Thr Ser Asp Tyr Ala Gln Lys Phe
    50                  55                  60

Gln Gly Arg Val Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Met Gly Val Thr His Ser Tyr Val Met Asp Ala Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205
```

```
Pro Ser Asn Thr Lys Val Asp Lys Val Glu Pro Lys Ser Cys Asp
    210                 215                 220

Lys Thr His Thr Cys Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 12
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Pro Ile Ser Ile Ser
            20                  25                  30

Val His Trp Tyr Gln Gln Lys Pro Gly Gln Ala Pro Arg Leu Leu Ile
        35                  40                  45

Tyr Phe Ala Ser Gln Ser Ile Ser Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Thr Phe Ser Leu Pro Tyr
                85                  90                  95

Thr Phe Gly Gln Gly Thr Lys Val Glu Ile Lys Arg Thr Val Ala Ala
            100                 105                 110
```

Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 13
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 13

| | | | | | |
|---|---|---|---|---|---|
| caggtgcagc | tggtgcagtc | tggcgccgaa | gtgaagaaac | ctggcgcctc | cgtgaaggtg | 60 |
| tcctgcaagg | cctccggcta | catcttcacc | gactacgcca | tgcactgggt | ccgccaggct | 120 |
| ccaggacagg | gcctggaatg | gatgggcacc | ttcatccctc | tgctggacac | ctctgactac | 180 |
| gcccagaaat | tccagggcag | agtgaccatg | accgccgaca | cctccacctc | caccgcctac | 240 |
| atggaactgc | ggtccctgag | atccgacgac | accgccgtgt | actactgcgc | ccggatgggc | 300 |
| gtgacacact | cctacgtgat | ggacgcttgg | ggccagggca | ccctggtcac | cgtgtcctcc | 360 |
| gctagcacca | agggcccttc | cgtgttccct | ctggccccct | cctccaagtc | tacctctggc | 420 |
| ggcaccgctg | ctctgggctg | tctggtcaag | gactacttcc | ctgagcctgt | gacagtctct | 480 |
| tggaactctg | gcgccctgac | ctccggcgtg | cacaccttcc | ctgccgtgct | gcagtctagt | 540 |
| ggcctgtact | ccctgtcctc | cgtggtcaca | gtgccttcat | catccctggg | cacccagacc | 600 |
| tacatctgca | acgtgaacca | caagccttcc | aacaccaagg | tggacaagaa | ggtggagcct | 660 |
| aagtcctgcg | acaagaccca | cacctgtcct | ccatgccctg | ccctgagct | gctgggcgga | 720 |
| ccctccgtgt | tcctgttccc | tcctaagcct | aaggacaccc | tgatgatctc | ccggacccct | 780 |
| gaagtgacct | gcgtggtggt | ggacgtgtcc | cacgaggacc | cagaagtgaa | gttcaattgg | 840 |
| tacgtggacg | gcgtggaggt | gcacaacgcc | aagaccaagc | ctcgggagga | acagtacaac | 900 |
| tccacctacc | gggtggtgtc | cgtgctgacc | gtgctgcacc | aggactggct | gaacggcaaa | 960 |
| gaatacaagt | gcaaggtgtc | caacaaggcc | ctgcctgccc | ctatcgaaaa | gaccatctcc | 1020 |
| aaggccaagg | gccagccaag | agaacctcag | gtgtacaccc | tgcctccctc | cgggacgag | 1080 |
| ctgaccaaga | accaggtgtc | cctgacatgc | ctggtcaagg | gcttctaccc | ttccgatatc | 1140 |
| gccgtggagt | gggagtctaa | cggccagcct | gagaacaact | acaagaccac | ccctcctgtg | 1200 |
| ctggactccg | acggctcctt | cttcctgtac | tccaagctga | ccgtggacaa | gtcccggtgg | 1260 |
| cagcagggca | acgtgttctc | ctgctccgtg | atgcacgagg | ccctgcacaa | ccactacacc | 1320 |
| cagaagtccc | tgtccctgtc | tcctggcaag | | | | 1350 |

<210> SEQ ID NO 14
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 14

```
gagatcgtgc tgacccagtc ccctggcacc ctgtctctgt ctcccggcga gagagccacc    60
ctgtcctgcc gggcctccca gcctatctcc atctccgtgc actggtatca gcagaagcca   120
ggacaggccc ctcggctgct gatctacttc gcttctcagt ctatctctgg catccctgac   180
cggttctccg gctctggctc cggcaccgac ttcaccctga ccatctcccg gctggaacct   240
gaggacttcg ccgtgtacta ctgccagcag accttctccc tgccttacac cttcggccag   300
ggcaccaagg tggagatcaa gcgtacggtg gccgctcctt ccgtgttcat cttccctccc   360
tccgacgagc agctgaagtc cggcaccgcc tctgtcgtct gcctgctgaa caacttctac   420
cctcgggagg ccaaggtgca gtggaaggtg acaacgccc tgcagtccgg caactcccag   480
gaatccgtca ccgagcagga ctccaaggac tctacctact ccctgtcctc caccctgacc   540
ctgtccaagg ccgactacga gaagcacaag gtgtacgcct gcgaagtgac ccaccagggc   600
ctgtcatctc cagtgactaa gtctttcaac cggggcgagt gc                      642
```

<210> SEQ ID NO 15
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 15

Met Ala Val Leu Gly Leu Leu Phe Cys Leu Val Thr Phe Pro Ser Cys
1               5                   10                  15

Val Leu Ser

<210> SEQ ID NO 16
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 16

Met Ala Pro Val Gln Leu Leu Gly Leu Leu Val Leu Phe Leu Pro Ala
1               5                   10                  15

Met Arg Cys

What is claimed is:

1. A binding compound that specifically binds human TSLP comprising:
an antibody heavy chain variable region or a TSLP-binding fragment thereof, said heavy chain variable region comprising: a CDR-H1 sequence comprising SEQ ID NO:1, a CDR-H2 sequence comprising SEQ ID NO:2, and a CDR-H3 sequence comprising SEQ ID NO:3; and
an antibody light chain variable region or a TSLP-binding fragment thereof, said light chain variable region comprising: a CDR-L1 sequence comprising SEQ ID NO:4, a CDR-L2 sequence comprising SEQ ID NO:5, and a CDR-L3 sequence comprising SEQ ID NO:6.

2. The binding compound of claim 1, wherein the heavy chain variable region comprises the amino acid sequence of SEQ ID NO:7.

3. The binding compound of claim 1, wherein the light chain variable region comprises the amino acid sequence of SEQ ID NO:8.

4. The binding compound of claim 1, wherein the heavy chain variable region comprises the amino acid sequence of SEQ ID NO:7 and the light chain variable region comprises the amino acid sequence of SEQ ID NO:8.

5. The binding compound of claim 1, wherein the binding compound is an antibody comprising SEQ ID NO:11 and SEQ ID NO:12.

6. The binding compound of claim 1, wherein the binding compound can be expressed from the vector deposited under ATCC Deposit No. PTA-10482.

7. The binding compound of claim 1, wherein the binding compound is a humanized antibody or a TSLP-binding fragment thereof.

8. The binding compound of claim 1, wherein the binding compound is a TSLP-binding antibody fragment selected from the group consisting of Fab, Fab', Fab'-SH, Fv, scFv, F(ab')$_2$, and a diabody.

9. A composition comprising the binding compound of claim 1 in combination with a pharmaceutically acceptable carrier or diluent.

10. An isolated nucleic acid encoding an antibody or an antigen-binding fragment thereof that specifically binds human TSLP, wherein the heavy chain variable region of the antibody comprises a CDR-H1 sequence comprising SEQ ID NO:1, a CDR-H2 sequence comprising SEQ ID NO:2, and a CDR-H3 sequence comprising SEQ ID NO:3; and the light chain variable region of the antibody comprises a CDR-L1 sequence comprising SEQ ID NO:4, a CDR-L2 sequence comprising SEQ ID NO:5, and a CDR-L3 sequence comprising SEQ ID NO:6.

11. An expression vector comprising the nucleic acid of claim 10.

12. An isolated host cell comprising the expression vector of claim 11.

13. A method of producing an antibody encoded by the nucleic acid of claim 10 comprising:

culturing a host cell transformed with an expression vector comprising said nucleic acid under conditions wherein the nucleic acid is expressed thereby producing said antibody; and recovering said antibody from the host cell or culture medium.

14. The expression vector deposited under ATCC Deposit No. PTA-10482.

15. An isolated host cell comprising the expression vector of claim 14.

\* \* \* \* \*